United States Patent
Trudeau et al.

(10) Patent No.: US 8,231,676 B2
(45) Date of Patent: Jul. 31, 2012

(54) MOTION PRESERVING ARTIFICIAL INTERVERTEBRAL DISC DEVICE

(75) Inventors: Jeffrey L. Trudeau, Marquette, MI (US); Qi-Bin Bao, Marquette, MI (US); Brian Janowski, Marquette, MI (US); Weston Pernsteiner, Marquette, MI (US); Tim Brown, Negaunee, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 176 days.

(21) Appl. No.: 12/436,032

(22) Filed: May 5, 2009

(65) Prior Publication Data

US 2009/0240333 A1    Sep. 24, 2009

Related U.S. Application Data

(63) Continuation-in-part of application No. 11/856,667, filed on Sep. 17, 2007.

(60) Provisional application No. 61/050,612, filed on May 5, 2008.

(51) Int. Cl.
*A61F 2/44* (2006.01)

(52) U.S. Cl. ............... 623/17.11; 623/17.13; 623/17.15; 623/17.16

(58) Field of Classification Search ..... 623/17.13–17.15
See application file for complete search history.

(56) References Cited

U.S. PATENT DOCUMENTS

| | | | |
|---|---|---|---|
| 4,636,217 A | 1/1987 | Ogilvie et al. | |
| 4,759,769 A * | 7/1988 | Hedman et al. | 623/17.13 |
| 5,123,926 A | 6/1992 | Pisharodi | |
| 5,314,477 A | 5/1994 | Marnay | |
| 5,425,773 A | 6/1995 | Boyd et al. | |
| 5,507,816 A | 4/1996 | Bullivant | |
| 5,676,701 A | 10/1997 | Yuan | |
| 5,888,226 A | 3/1999 | Rogozinski | |

(Continued)

FOREIGN PATENT DOCUMENTS

CA       2548780        7/2005

(Continued)

OTHER PUBLICATIONS

International Searching Authority, International Search Report dated Apr. 23, 2008, from corresponding International Patent Application No. PCT/US2007/078679, 3 pp.

(Continued)

*Primary Examiner* — Thomas J Sweet
*Assistant Examiner* — Brian Dukert
(74) *Attorney, Agent, or Firm* — Fitch, Even, Tabin & Flannery, LLP

(57) ABSTRACT

A motion preserving implant having first and second bearing members and a biasing member disposed therebetween operable to provide resistance to the translation of the bodies with respect to one another. An intervertebral implant having first and second bearing members, a translatable member, a resilient connection between the translatable member and one of the bearing members to allow for relative motion therebetween and bearing surfaces of the translatable member and the other bearing member to allow complex, natural motion between the bearing members. A spinal implant having upper and lower bodies and an articulation surface that allows for polyaxial articulation and translation through a concave articulation surface having a first radius of curvature and a second radius of curvature in at least one plane, and a convex articulation surface having the first radius of curvature in the same plane.

18 Claims, 15 Drawing Sheets

U.S. PATENT DOCUMENTS

| | | | |
|---|---|---|---|
| 6,039,763 | A | 3/2000 | Shelokov |
| 6,146,421 | A | 11/2000 | Gordon et al. |
| 6,210,442 | B1 | 4/2001 | Wing et al. |
| 6,371,987 | B1 | 4/2002 | Weiland et al. |
| 6,540,785 | B1 | 4/2003 | Gill |
| 6,610,093 | B1 | 8/2003 | Pisharodi |
| 6,767,367 | B1 | 7/2004 | Michelson |
| 6,770,096 | B2 | 8/2004 | Bolger et al. |
| 6,923,830 | B2 | 8/2005 | Michelson |
| 6,926,737 | B2 | 8/2005 | Jackson |
| 6,936,071 | B1 | 8/2005 | Marnay et al. |
| 6,981,975 | B2 | 1/2006 | Michelson |
| 7,056,341 | B2 | 6/2006 | Crozet |
| 7,074,240 | B2 | 7/2006 | Pisharodi |
| 7,662,182 | B2 | 2/2010 | Zubok et al. |
| 7,682,397 | B2 * | 3/2010 | Berry et al. ............ 623/17.14 |
| 7,794,465 | B2 | 9/2010 | Marik et al. |
| 7,819,920 | B2 | 10/2010 | Assaker |
| 8,038,678 | B2 | 10/2011 | Schmieding et al. |
| 2002/0035400 | A1 | 3/2002 | Bryan et al. |
| 2002/0165613 | A1 | 11/2002 | Lin et al. |
| 2004/0006394 | A1 | 1/2004 | Lipman et al. |
| 2004/0044410 | A1 | 3/2004 | Ferree et al. |
| 2004/0093082 | A1 | 5/2004 | Ferree |
| 2004/0243240 | A1 | 12/2004 | Beaurain et al. |
| 2005/0038515 | A1 | 2/2005 | Kunzler |
| 2005/0071010 | A1 | 3/2005 | Crozet |
| 2005/0080488 | A1 * | 4/2005 | Schultz ............... 623/17.13 |
| 2005/0273166 | A1 | 12/2005 | Sweeney |
| 2006/0004453 | A1 | 1/2006 | Bartish |
| 2006/0020341 | A1 | 1/2006 | Schneid et al. |
| 2006/0085076 | A1 * | 4/2006 | Krishna et al. ............ 623/17.15 |
| 2006/0095136 | A1 | 5/2006 | McLuen |
| 2006/0116767 | A1 | 6/2006 | Magerl et al. |
| 2006/0178744 | A1 | 8/2006 | de Villiers et al. |
| 2006/0178745 | A1 | 8/2006 | Bartish, Jr. et al. |
| 2006/0195191 | A1 | 8/2006 | Sweeney et al. |
| 2006/0212122 | A1 | 9/2006 | Perera |
| 2006/0293752 | A1 | 12/2006 | Moumene et al. |
| 2007/0055376 | A1 | 3/2007 | Michelson |
| 2007/0100455 | A1 | 5/2007 | Parsons |
| 2007/0270961 | A1 | 11/2007 | Ferguson |
| 2007/0288005 | A1 | 12/2007 | Arnin et al. |
| 2008/0103598 | A1 | 5/2008 | Trudeau et al. |
| 2010/0016974 | A1 | 1/2010 | Janowski et al. |
| 2010/0280619 | A1 | 11/2010 | Yuan et al. |

FOREIGN PATENT DOCUMENTS

| | | | |
|---|---|---|---|
| DE | 29612269 | U1 | 10/1996 |
| DE | 19816832 | C1 | 1/2000 |
| WO | 2006016384 | | 2/2006 |

OTHER PUBLICATIONS

International Searching Authority, International Search Report dated Jun. 22, 2009, from corresponding International Patent Application No. PCT/US2009/042882, 2 pp.

* cited by examiner

MOTION PRESERVING ARTIFICIAL INTERVERTEBRAL DISC DEVICE

RELATED APPLICATIONS

This application is a continuation-in-part of U.S. patent application Ser. No. 11/856,667, filed Sep. 17, 2007, and claims the benefit of U.S. Provisional Patent Application No. 61/050,612, filed May 5, 2008, both of which are incorporated herein by reference in their entirety.

FIELD OF THE INVENTION

The invention relates to motion preserving artificial implants for weight bearing joints, and, more particularly, to motion preserving artificial intervertebral disc implants having components that include an articulating interface therebetween.

BACKGROUND OF THE INVENTION

Joint degeneration is a common problem that can occur in a variety of joints throughout the human body. The condition typically is more prevalent as the skeletal system ages and is often treated with medications and/or physical therapy. These conservative treatments sometimes meet only limited success. If unsuccessful, the patient typically will continue to experience ongoing pain and limited mobility.

Often the treatment progression leads to a total joint replacement. These replacements have been performed for years in joints such as the hip and the knee. The replacement devices usually comprise some form of a metallic structural component or endplate with an intermediate polyethylene core. It is not unusual for replacements such as these to give 15-20 years of service before requiring some degree of revision.

In the spine, the surgical treatment of choice has been fusion for the treatment of intervertebral disc degeneration. The spinal intervertebral disc is situated between the vertebral bodies. The spinal disc is comprised of a tough outer ring called the annulus, and a jelly-like filling called the nucleus. The belief has been that removing the diseased spinal disc(s) and fusing between affected levels will not make a significant difference in the overall mobility of the spine. However, spinal fusion has proved to cause an increase in degeneration at other vertebral levels that must compensate for the loss of motion at the fused level commonly causing the patient to relapse into more pain and limited mobility.

Recently, there has been a focus on the use of "motion preservation" implants over implants that promote spinal fusion. These motion preserving implants, in the form of joint replacements in the spine, show promise to alleviate many of the problems associated with fusion devices in the spine. Intervertebral disc replacement devices are seen today typically comprising a pair of biocompatible metal plates with a polymer or elastomeric core, or a metal plate articulating on a metal plate. Some known implants incorporate springs to provide shock absorption or resistance to compression of the joint in a direction normal to the transverse axis of the spine. However, current motion preserving implants have certain disadvantages relating to range of motion, stability, and comfort.

Load-bearing implants, and in particular, intervertebral implants that preserve motion between the vertebral bones in the joint have been found to be preferable to fusion members in many circumstances. Specifically, to more closely mimic a healthy, natural intervertebral joint, such implants provide not only for polyaxial rotation between the vertebrae, but also for small amounts of translation therebetween. This translation is sometimes required when the vertebral joint is in extension, such as when the spine is bent backwards. Previously known implants developed to allow for both polyaxial rotation and translation have drawbacks, including high wear rates, unnatural or unsafe dynamics, and complex implantation and removal procedures. The following embodiments overcome these and other drawbacks of currently known implants.

SUMMARY OF THE INVENTION

In accordance with one aspect of the present invention, a motion preserving implant device is provided with a biasing member to allow for an increased range of articulated motion between implant components. The biasing member allows a translatable member of the implant device to resiliently shift, such as with respect to a fixed member of the implant. In a preferred form, guide structure between the translatable and fixed member causes resilient shifting of the translatable member in a predetermined linear direction, such as in a fore-and-aft or anterior-posterior direction.

In another form of the invention, the implant device has upper and lower implant members that are each provided with fixing structure for securing the members to respective adjacent upper and lower vertebrae. An arcuate bearing interface is provided between the upper and lower implant members that are configured to allow both arcuate relative motion similar to a ball bearing, as well as translatory relative motion between the upper and lower implant members. To increase the range of translatory motion, the lower implant member is provided with a translatable member.

The translatable member is preferably provided with a bearing interface, such that the implant may articulate independently of the resilient shifting of the translatable member. In one form, the articulation surface is a convex, arcuate shape which interacts with a corresponding concave articulation surface on one of the implant bodies. This articulation interface allows polyaxial articulation of the implant, which mimics the natural range of motion of an intervertebral disc. By allowing the articulation surface to translate along with the translatable member, the range of motion of the implant may be further increased. At the same time, the biasing member operates to increase the stability of the implant by resisting movement of the translatable member and returning the translatable member to its initial position as translating forces are removed therefrom.

Abrupt stops in movement of the implant can be uncomfortable, painful, or even dangerous for the patient. Further, such stops can damage the implant, causing further complications for the patient. In a motion preserving implant, such as an intervertebral implant, abrupt stops in translation can be avoided by implementation of the biasing member. The translatable member follows a path provided by guide structure such as a tongue and groove, channel, rail, track, or other structure to guide the body. To provide limits to the range of motion of the translatable member, stop members are provided. The stop members may be formed on the translatable member or on an implant body itself, or the stops may be in the form of a separate member associated with the guide structure. In addition, stop members may be provided on both the translatable body and the implant body, such that the interaction between the stops limits the motion of the translatable member. Preferably, the biasing member keeps the translatable body from contacting the stops with excessive force. Moreover, the biasing member may be operable to avoid or otherwise substantially limit contact between the stop members, such that the properties of the biasing member determine the limit of the range of motion of the translatable body.

An intermediate bearing member is disposed between the upper and lower implant members and forms an arcuate bearing interface with one of the implant members, such as the upper implant member. Linear guide structure is provided between the intermediate bearing member and the other one of the implant members, such as the lower implant member. The linear guide structure includes a guide projection and a narrow guide slot or channel into which the guide projection fits for translation therein. Preferably, the guide projection extends upwardly from the lower implant member into the guide channel formed in the bottom surface of the intermediate bearing member for linear translation therein. The guided articulation of the intermediate bearing member allows for a controlled, increased range of motion provided by the implant herein.

In a preferred form, the implant device provides for a controlled resistance to the guided articulation of the intermediate bearing member by way of a biasing member between the intermediate bearing member and the lower implant member. In this manner, the implant device provides for increasing resistance to linear travel prior to reaching the limits of the linear range of motion provided by the lower guide structure.

The biasing member may include an elongate spring member such as a flat or leaf spring and a spring supporting structure between the bearing member and lower implant member. The spring supporting structure can include a pair of guide projections spaced in the linear direction of travel of the bearing member and between which the spring member extends in a direction transverse, and preferably orthogonal to the linear travel direction. The supporting structure can further include a channel in the bottom of the bearing member extending transverse or orthogonal to the guide channel for receiving the spring member therein with the channels generally forming a cross configuration in the bottom of the bearing member. As is apparent, the spring supporting structure advantageously utilizes the linear guide structure in the form of the spaced guide projections that are received in the guide channel and which retain the spring member extending therebetween.

In another form in accordance with the present invention, an intervertebral implant for being inserted between adjacent upper and lower vertebrae includes an upper body, a lower body, and an articulation interface located between the upper and lower bodies. The articulation interface includes a concave articulating surface with a first portion having a first radius of curvature and a second portion having a second radius of curvature located in at least one plane, wherein the first radius of curvature is smaller than the second and neither of the first and second radii of curvatures are infinite; that is, neither of the first and second portions comprise flat surfaces. The articulation interface also includes a convex articulating surface having the first radius of curvature in the same plane as the plane in which the concave articulating surface has first and second radii of curvature. Preferably, the second radius of curvature is larger than the first. In such forms, the radius of curvature of the convex articulation surface is preferably the same as the first portion, which allows the convex articulation surface to translate along the second portion, which has a larger radius of curvature than the convex articulation surface. The convex and concave articulation surfaces thereby comprise the articulation interface, which provides for polyaxial rotation as well as translation of the upper and lower bodies with respect to each other. In this configuration, the implant provides for a more natural range of motion by allowing translational sliding of the implant bodies with respect to one another when the joint is in extension. For example, if the implant were implanted between cervical vertebrae in the user's neck, translational sliding of the implant bodies would be permitted by the implant when the user bends their head backwards.

In some forms, the concave articulating surface is disposed on the upper body. In addition, the convex surface articulating surface may be disposed on the lower body. In one form, the concave articulation surface has two different radii of curvature in the sagittal plane, such that the upper and lower bodies may translate with respect to each other in the anterior-posterior direction. Further, a posterior portion of the concave articulation surface may comprise the first radius of curvature and an anterior portion of the concave articulation surface may comprise the second radius curvature. In one embodiment the first and second radii intersect one another, such that concave articulation surface includes a line interface wherein the radius of curvature of the concave articulation surface changes between the first and second radius of curvature. The line interface may be located generally at a midpoint of the articulation interface, or generally at the shallowest portion of the concave articulation surface. The concave and convex articulation surfaces preferably have the same radii of curvature in a coronal plane.

In this configuration, the implant more clearly mimics the natural dynamics of a natural disc joint, by allowing the upper and lower implant bodies to pivot polyaxially, as well as translate with respect to each other. The articulation interface promotes self-centering due to the mating interaction between the concave and convex articulating surfaces, which advantageously keeps the implant bodies from becoming staggered or out of alignment. The implant also helps to keep the facet joints from being unnaturally loaded when the joint is in extension. In addition, wearing of the implant is reduced, because the articulation interface is smaller than that of an articulating interface having completely matching articulating surfaces. Reduced wear increases implant lifespan and reliability, and reduces complications caused by loose wear particles in and around the implantation site.

In another form of the invention, an intervertebral implant according to the present invention provides for improved load-bearing strength, ease of insertion, and securing strength via improved securing members. The securing members may have a leading end that is beveled or contoured in the insertion direction to ease insertion of the implant. In one form, the end of the rotary shaft of the securing member is beveled to keep the securing member from binding on an adjacent bone or surrounding tissue during insertion thereof. In addition, the leading retaining member, which is in mating engagement with the securing member, may similarly be beveled or contoured to ease insertion of the implant. With this configuration, the securing member and the retaining member are operable to distract the adjacent vertebra during insertion, rather than binding or digging into the adjacent bone or tissue.

The bone-engaging members of the securing members are preferably sized and configured to increase securing strength while allowing for sufficient material thickness of the implant body to maintain sufficient load-bearing strength. In particular, the bone-engaging members are large enough to provide sufficient contact area with the adjacent bone when the securing members are deployed. In addition, the securing members are preferably disposed on portions of the implant having increased axial thickness, such that the bone-engaging members may advantageously be disposed at least partially within the implant. Further, the bone-engaging members are sized to fit at least partially within the body of the bearing member when in the undeployed configuration without compromising the structural integrity of the implant. In one preferred form, the bone-engaging members of a single securing member may have varying sizes. In addition, the bone-engaging members of one securing member disposed on the implant may be of different size than the bone-engaging members of another securing member. In one form, two securing members are disposed on the upper bearing member and one securing member is disposed on the lower bearing member. The bone-engaging members of the lower securing member are larger compared to those of the upper for increased securing strength and to compensate for having only one securing member on the lower bearing member.

BRIEF DESCRIPTION OF THE DRAWINGS

To understand the present invention, it will now be described by way of example, with reference to the accompanying drawings in which.

DETAILED DESCRIPTION OF PREFERRED EMBODIMENTS

Figure 1:
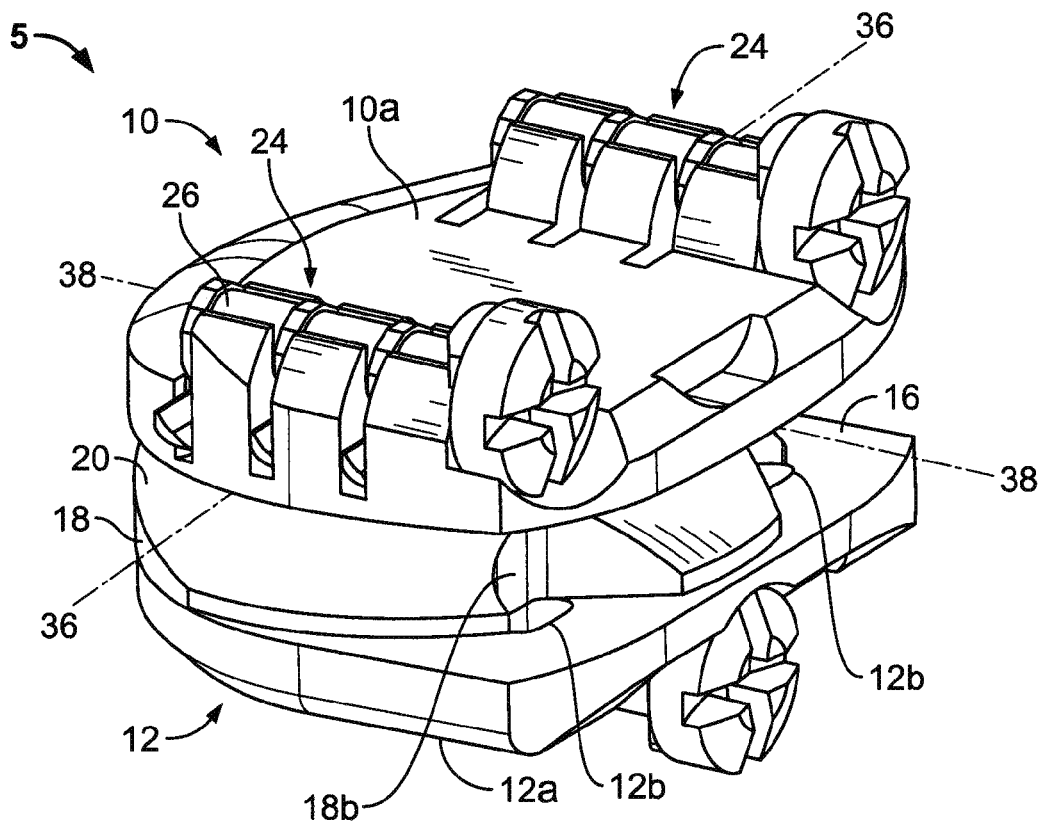
FIG. 1 is an anterolateral perspective view of an implant according to the present invention.
Figure 2:
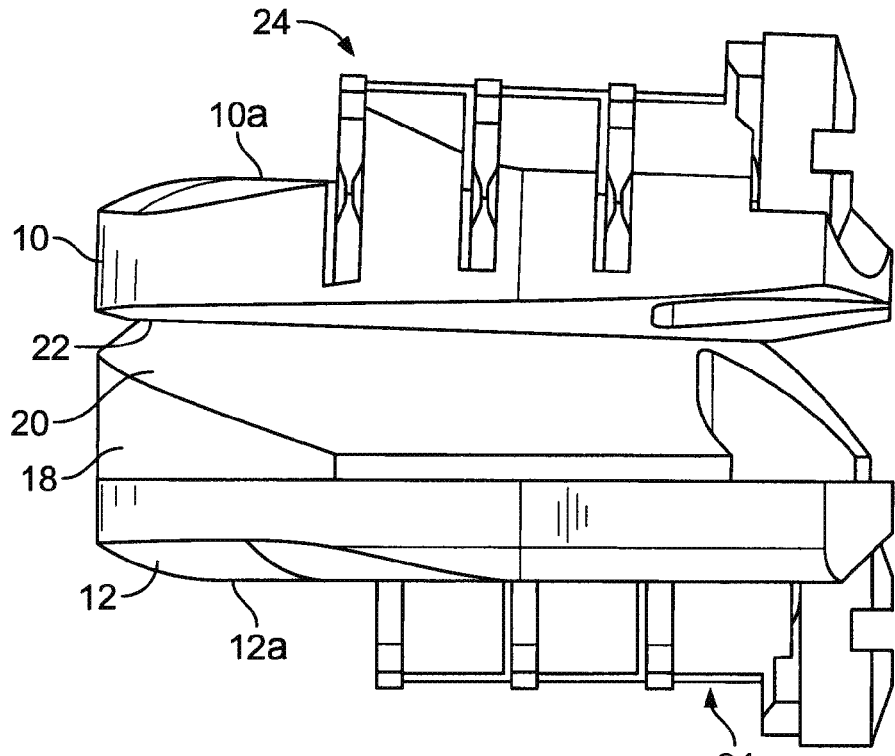
FIG. 2 is a side elevational view of the implant of FIG. 1.
Figure 3:
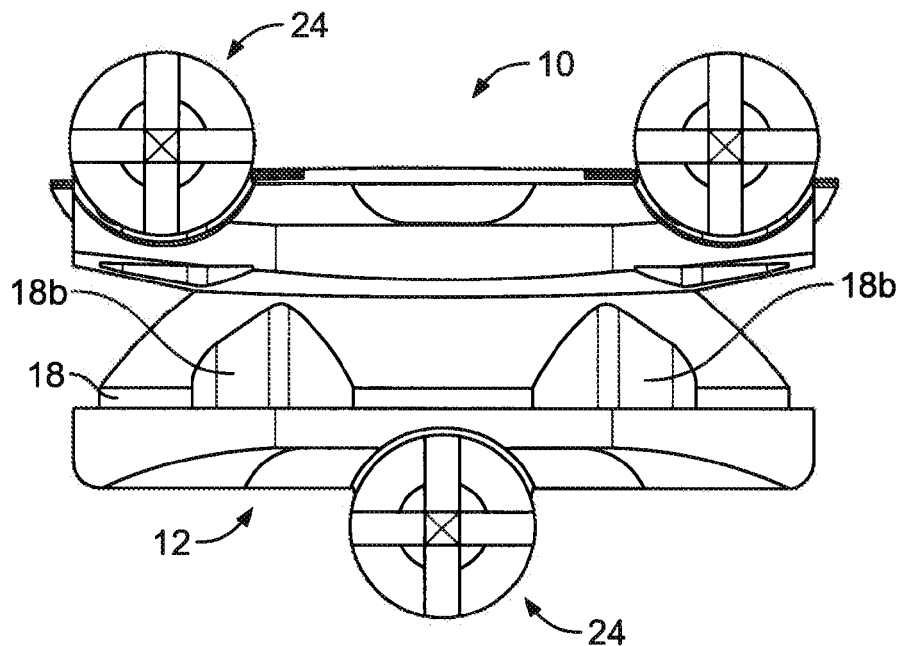
FIG. 3 is an anterior elevational view of the implant of FIG. 1.
Figure 4:
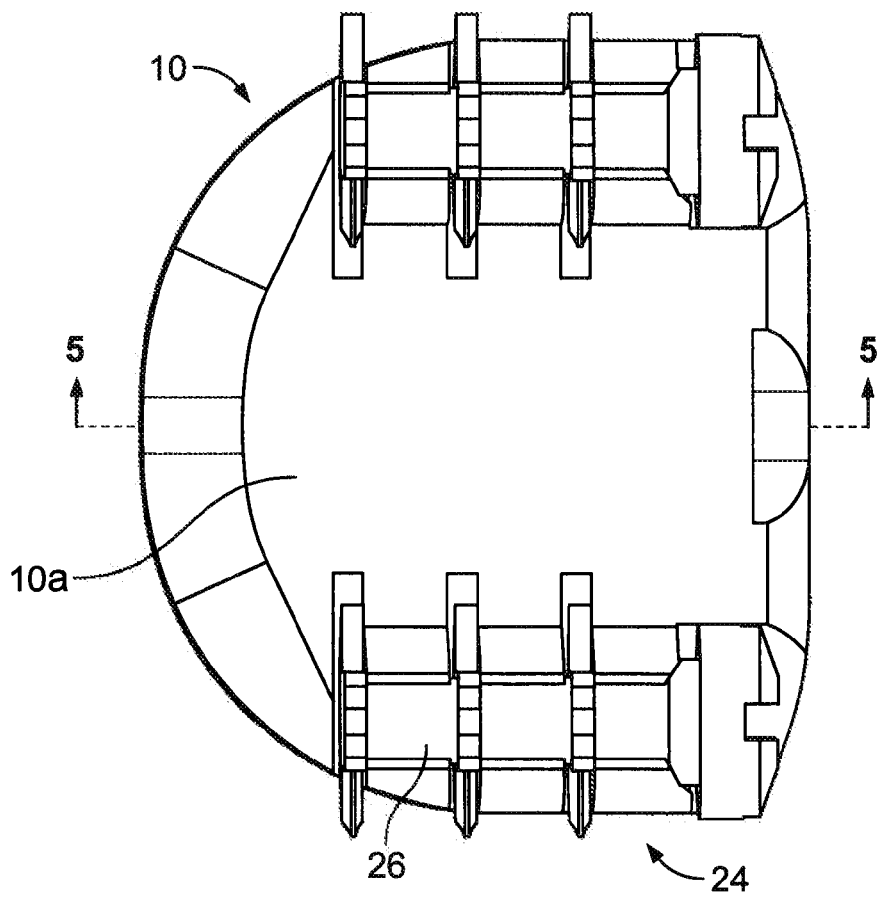
FIG. 4 is a top plan view of the implant of FIG. 1.

In a preferred embodiment, such as illustrated in FIGS. 1-16, an artificial disc device 5 comprises an upper implant body 10 and lower implant body 12. The upper body 10 comprises a substantially concave recess portion 14, as shown in FIG. 8, and the lower body 12 comprises a substantially flat interior portion 16, which extends generally in a transverse plane with respect to the patient as shown in FIG. 1, which may be defined by lateral axis 36 and anterior-posterior axis 38. A moveable member, such as a translatable member 18 is preferably provided between the upper and lower implant bodies 10, 12 to allow lateral movement between the bodies. Preferably, the translatable member may translate along the anterior-posterior axis 38, with the anterior side being illustrated on the right side of the page of FIG. 1 as it is implanted in the patient. The translatable member 18 may have a convex portion 20 disposed between the upper and lower implant bodies 10, 12 for providing an articulation interface 22 therebetween. The translatable member 18 is generally dome-shaped and has a generally flat lower surface 18a which interfaces with the flat interior portion 16 of the lower implant member 12. The translatable member 18 has contoured side walls 18b to provide clearance to the gripping portion of an inserter tool, such as that disclosed in U.S. patent application Ser. No. 11/856,667, which is incorporated herein by reference, which manipulates the implant within recesses 10b, 12b in the upper and lower implant bodies 10, 12. The gripping portion of the insertion tool preferably keeps the translatable member 18 from translating in an anterior direction during insertion of the implant 5 by providing an abutment surface against the side walls 18b. In a preferred form, the translatable member 18 is associated with the lower body 12. Although not preferred, the concave portion 14 and translatable member 18 may be switched such that the upper shell 10 may alternatively be associated with the translatable member 18. In the illustrated embodiments, the translatable member 18 is shown having a convex arcuate articulation surface disposed thereon. However, in other forms the translatable member may have different geometry for different applications, such as knee, hip, and ankle implants.

Figure 5:
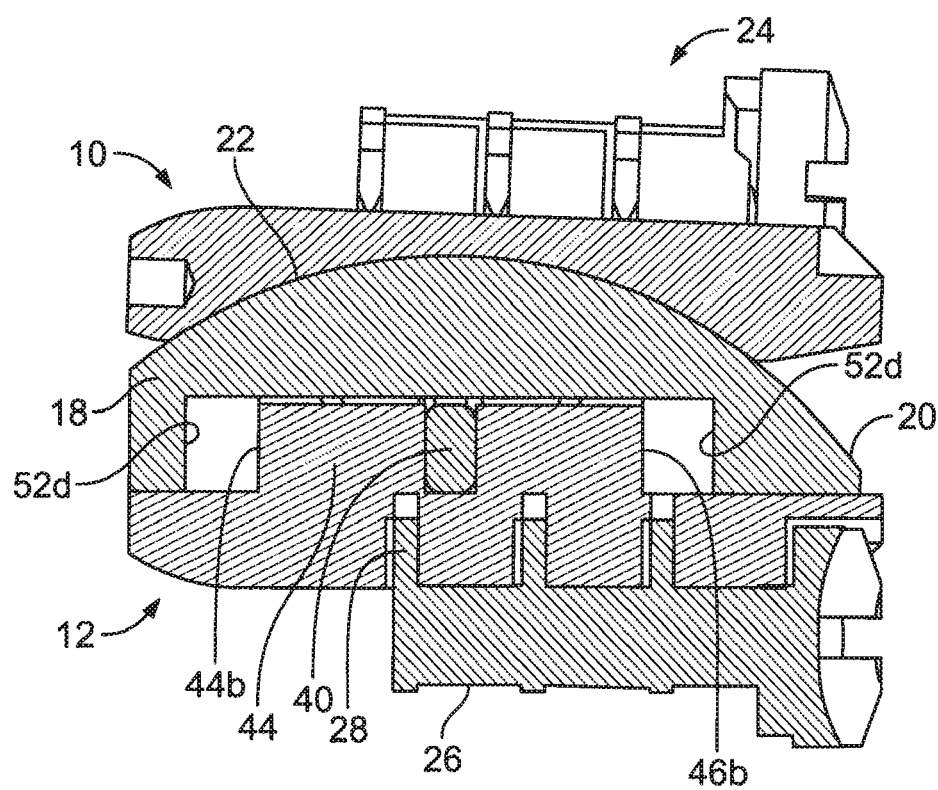
FIG. 5 is a side cross-sectional view of the implant of FIG. 1, illustrating the articulation interface, translatable member, and the biasing member.
Figure 6:
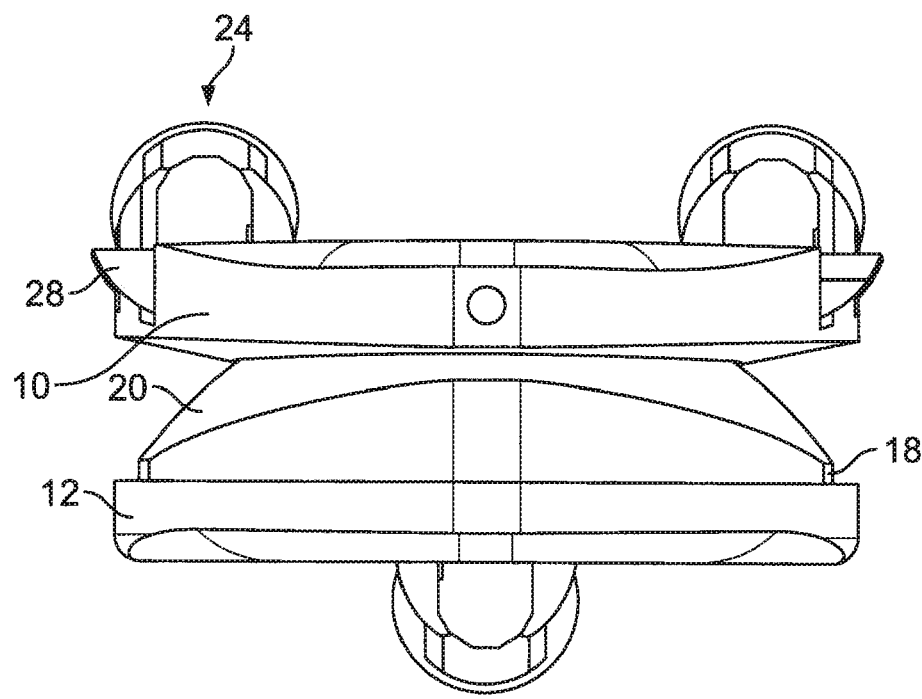
FIG. 6 is a posterior elevational view of the implant of FIG. 1.
Figure 7:
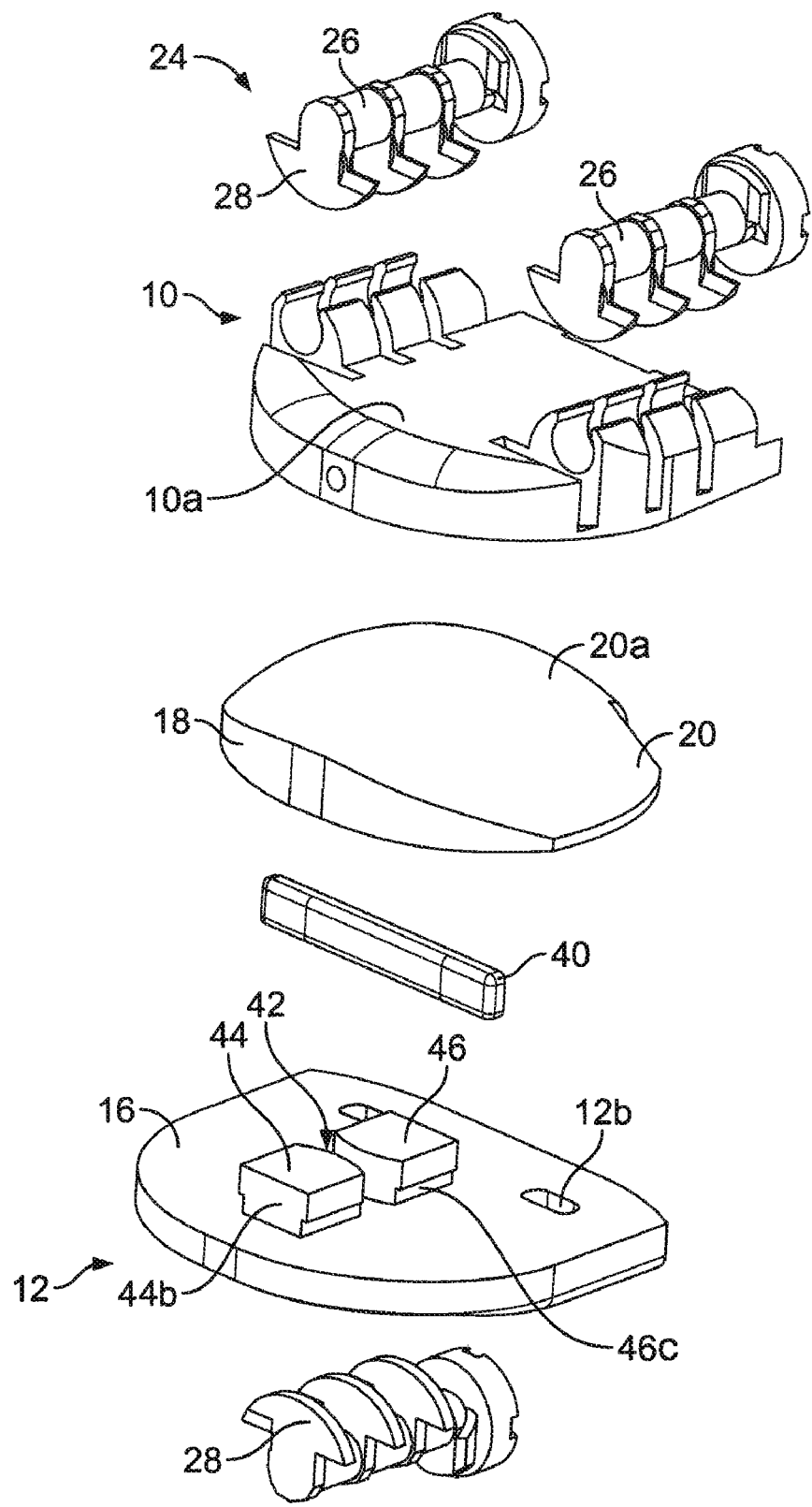
FIG. 7 is an exploded posterolateral perspective view of the implant of FIG. 1.
Figure 8:
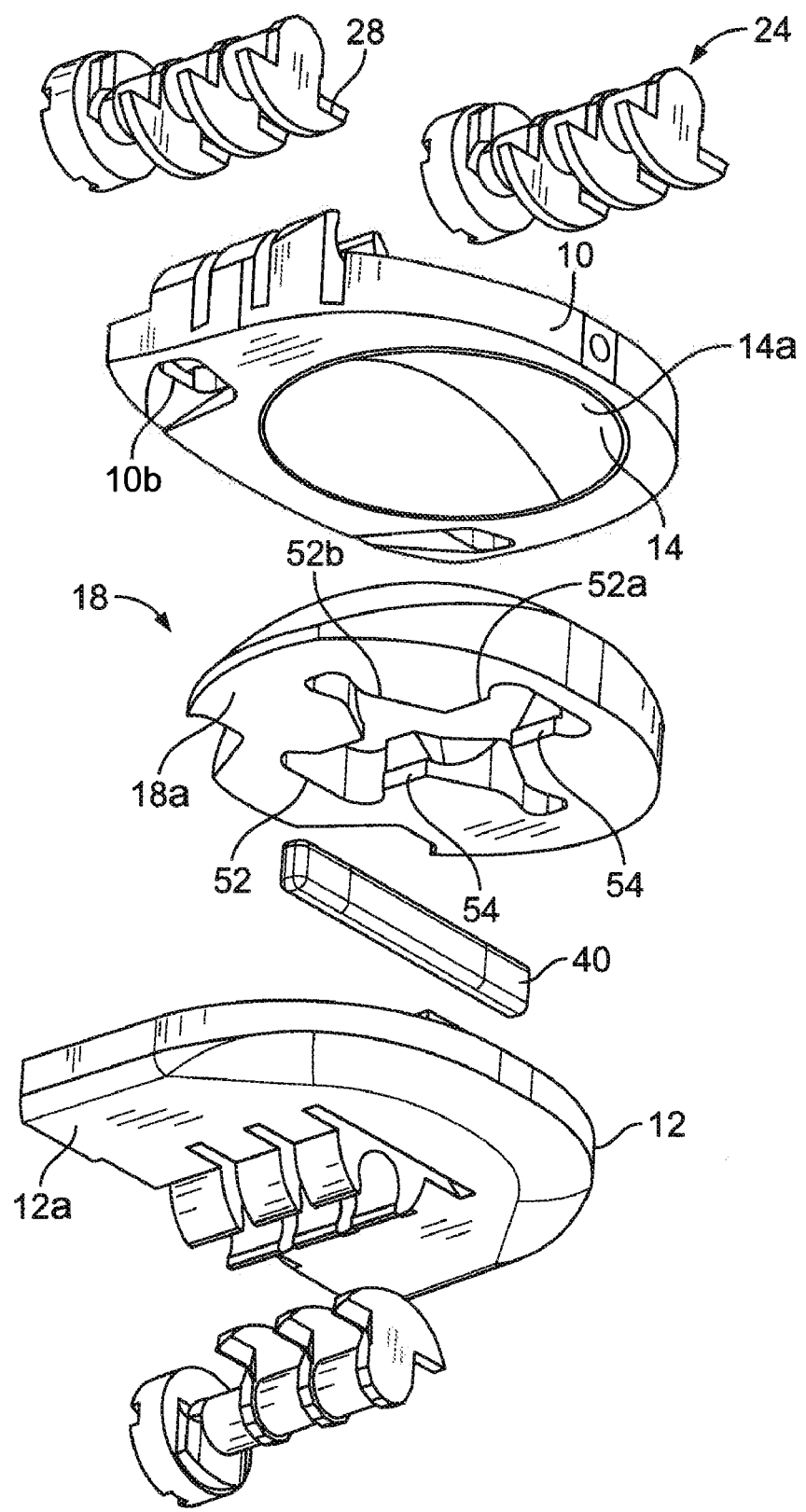
FIG. 8 is another exploded posterolateral perspective view of the implant of FIG. 1 showing other structural features.
Figure 9:
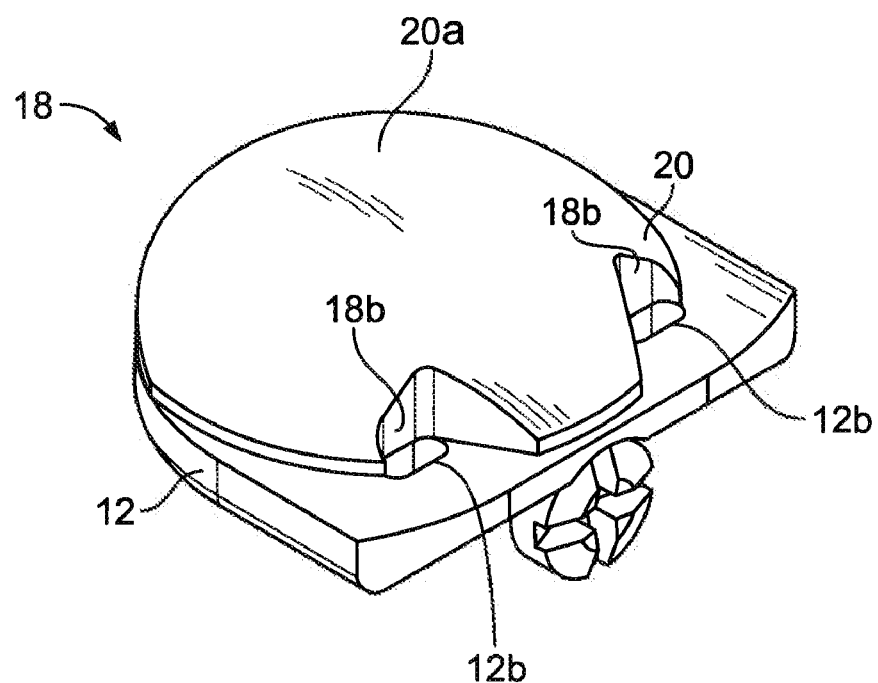
FIG. 9 is an anterolateral perspective view of the implant of FIG. 1 with the upper implant body hidden to show the translatable member.
Figure 22:
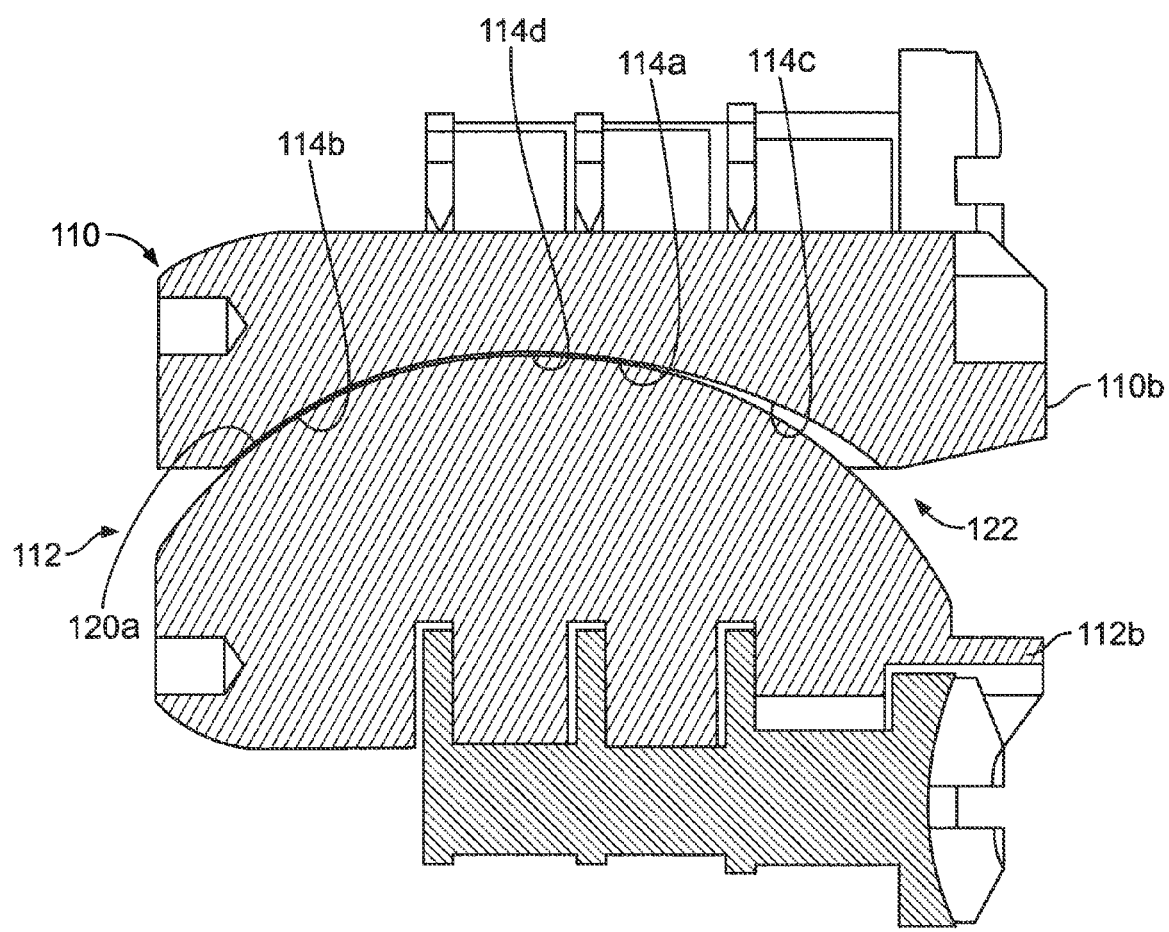
FIG. 22 is a cross-sectional view in the sagittal plane of the implant of FIG. 17 taken along the line 22-22 showing a posterior portion of the concave articulation surface having one radius of curvature in the sagittal plane and an anterior portion of the concave articulation surface having another, different radius of curvature.

As shown in FIGS. 5, 7 and 8, the convex portion 20 of the translatable member 18 comprises a convex articulation surface 20a, and the concave portion 14 comprises a concave articulation surface 14a. It is preferred that the articulation surfaces 20a and 14a have substantially matching geometries or radii of curvature, although some mismatch of curvature may be desired to provide a combination of rolling and sliding motion to occur between the articulation surfaces, as shown in FIG. 22 and described in more detail below. The geometries may be complex in nature but preferably are ball and socket style to allow polyaxial movement between the implant bodies 10, 12. The convex portion 20 and concave portion 14 may extend substantially to the outer perimeter of the bodies 10, 12 or may be formed with a smaller radius of curvature inward a predetermined distance from the outer perimeter of the bodies 10, 12. Each body 10, 12 is preferably manufactured from a PEEK material or a fiber reinforced PEEK or other biocompatible polymer combination or radiolucent material demonstrating very low surface wear in high repetition wear testing.

The artificial disc device 5 preferably comprises one or more restraint portion(s) 24 or structure located on one or both of the implant bodies 10, 12 to help prevent the bodies 10, 12 from becoming dislodged or migrating across the boney endplate of the vertebrae after insertion. For example, the restraining portion 24 may comprise a securing mechanism, such as a cam shaft 26 with radially extending protrusions, such as cam lobes 28. The restraining portion of the artificial disc 5 may take a variety of forms, including any of the embodiments disclosed in U.S. patent application Ser. No. 11/856,667. The restraining portion may be located on one or both of the implant bodies 10, 12, preferably on the endplate facing surfaces 10a, 12a. Although the securing mechanisms 24 are shown protruding from the endplate facing surfaces 10a, 12a, they may also be disposed completely within the upper or lower bodies 10, 12 to reduce the insertion profile of the implant 5 or to simplify preparation of the implant site prior to insertion of the implant.

It is preferred that the footprint of the artificial disc device 5 be similar to the footprint of the endplate, although generally smaller to fit within the intervertebral space. The endplate facing surfaces 10a, 12a are preferably contoured to match the contour of the endplates. For example, if the surgeon prepares the endplates to be flat, it is preferred that the endplate facing surfaces 10a, 12a are also flat. Likewise, if the endplates are prepared to be concave, it is preferred that the endplate facing surfaces 10a, 12a are similarly convex. It should be noted that endplates that are concave will generally retain the artificial disc device 5 better since the device 5 becomes cupped between the vertebrae.

In one form according to the present invention, the implant includes first and second bodies that are operably connected to one another such that they may translate with respect to one another. A biasing member is disposed between the first and second implant bodies, and is operably connected to at least one of the bodies to provide resistance to the translation of the bodies with respect to one another. As the implant bodies are translated with respect to one another, the biasing member provides a returning force that counteracts the translation of the bodies and causes at least one of the bodies to return to its initial position. In other words, the biasing member urges at least one of the first and second bodies back to their respective starting positions, and thereby provides a self-centering feature. Generally, the initial orientation of the implant bodies corresponds to a neutral orientation, i.e., an unflexed or unextended condition of the user's joint. Therefore, the implant bodies may translate when the user causes flexion or extension of the joint, and the self-centering feature of the implant will automatically return the implant bodies to their initial orientation when the joint is returned to its neutral position. In this form, the implant may be provided with or without a translatable member.

Figure 11:
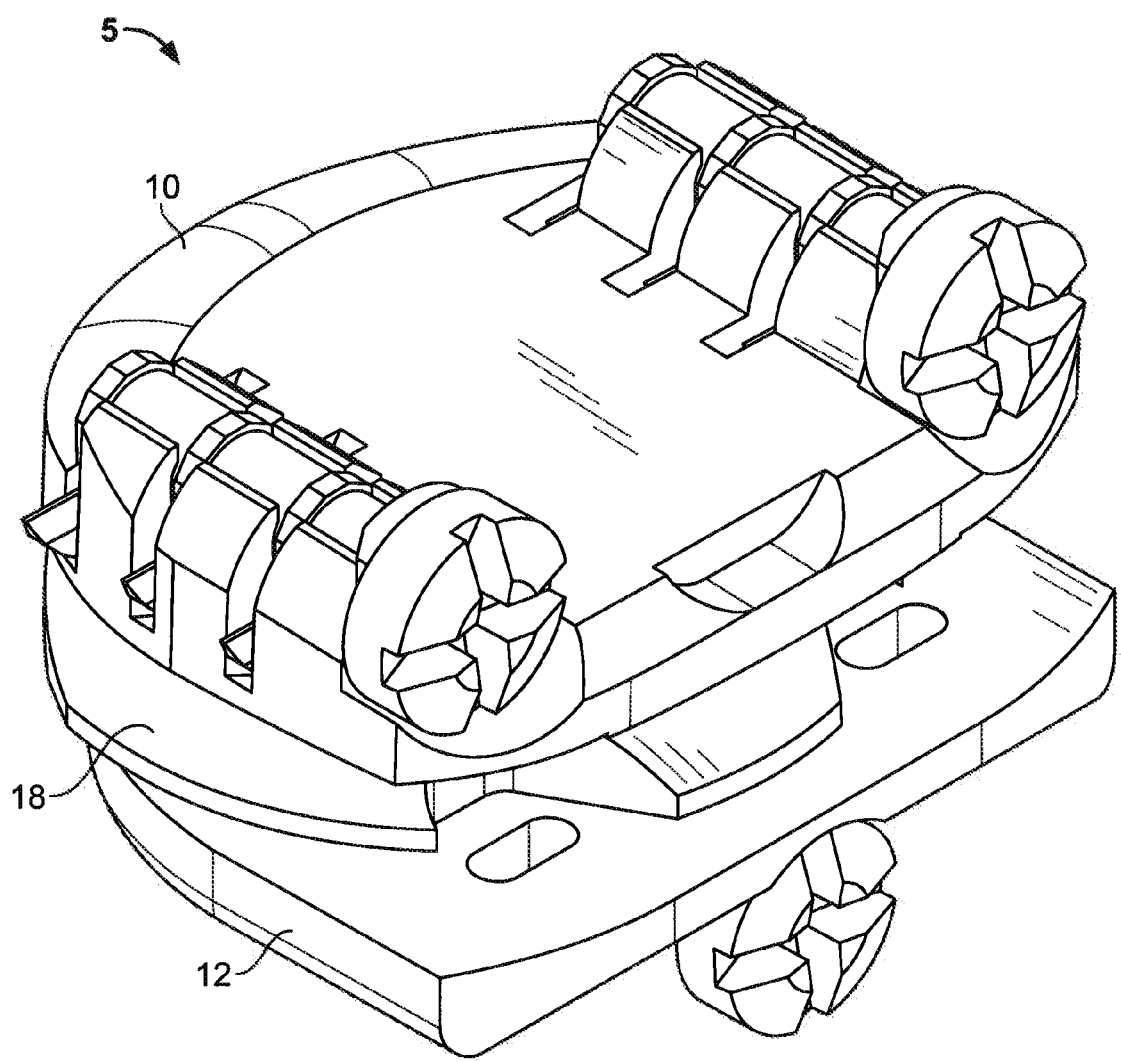
FIG. 11 is an anterolateral perspective view of the implant of FIG. 1 with the upper implant body and translatable member translated posteriorly with respect to the lower implant body.
Figure 12:
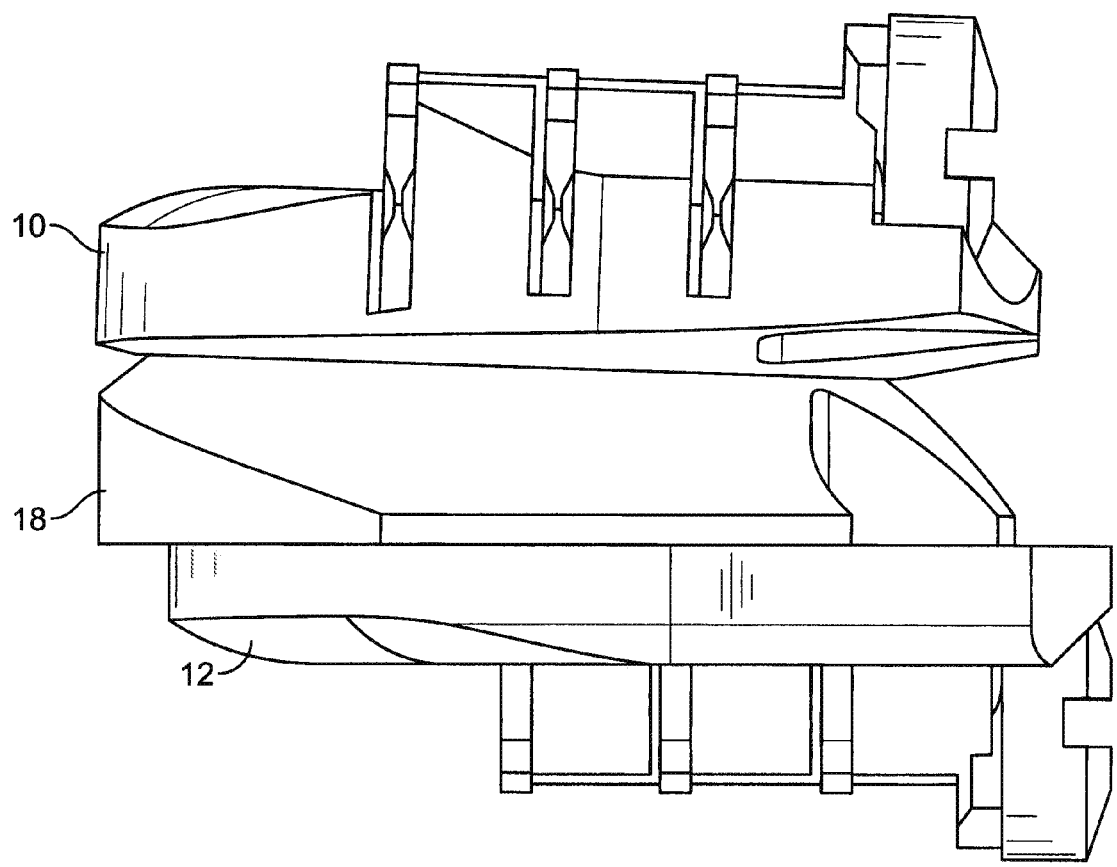
FIG. 12 is a side elevational view of the implant of FIG. 11.
Figure 13:
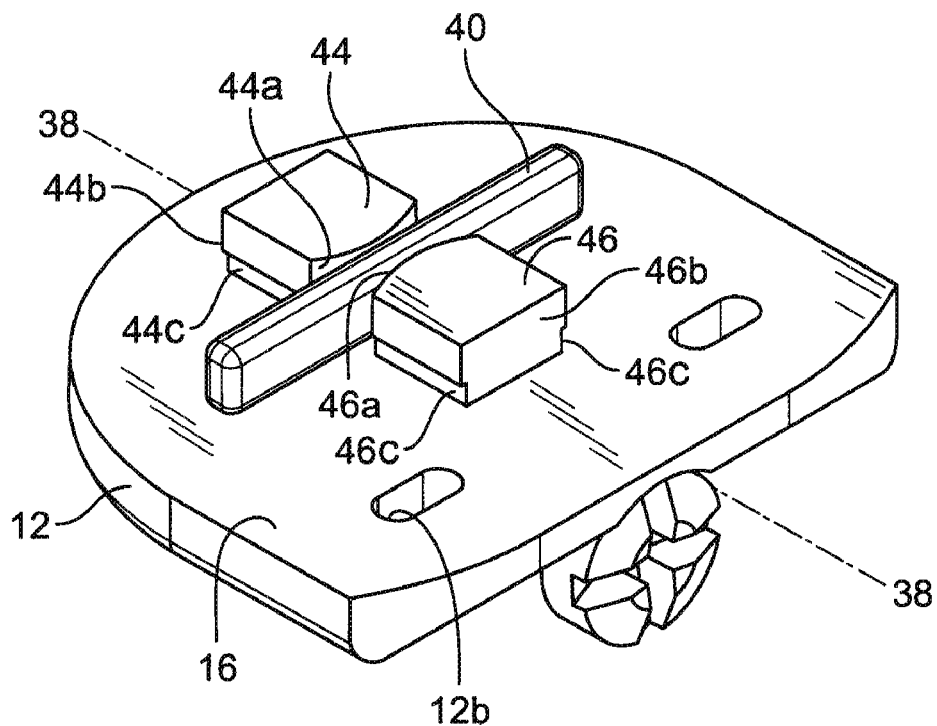
FIG. 13 is an anterolateral perspective view of the implant of FIG. 1 with the upper implant body and translatable member hidden to show the biasing member and associated structure of the lower implant body.
Figure 14:
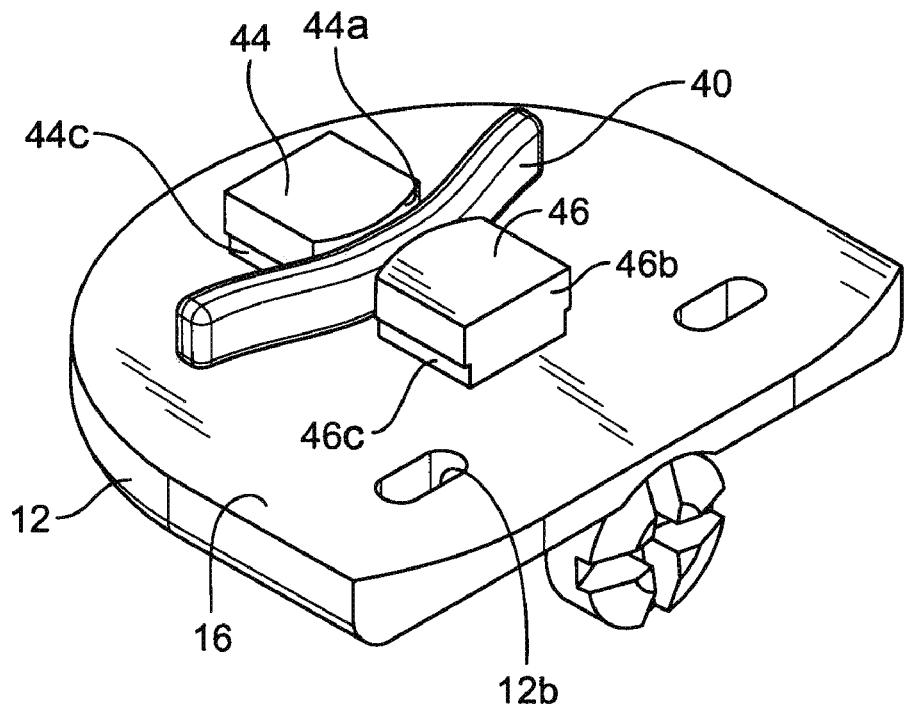
FIG. 14 is an anterolateral perspective view of the implant of FIG. 13 showing the biasing member in a flexed or biased orientation corresponding with the translation of the upper implant body and translatable member as shown in FIGS. 11 and 12.

In a preferred form shown in FIGS. 7-16 the biasing member takes the form of a resilient member such as a spring 40. The spring 40 is preferably made of a Nickel-titanium mixture, such as nitinol, or a titanium 6-4 alloy, but may be made of any suitable resilient material. The spring 40 is operably connected to the lower implant body 12. As shown in FIGS. 7 and 13, the spring 40 is received within a channel 42 formed by two protruding bodies, such as bosses 44, 46 on the upper, inner facing surface 16. The inner facing surfaces 44a, 46a of the bosses 44, 46 preferably have an arcuate shape to approximate the contour of the spring 40 as it is flexed during translation of the translatable member 18. These surfaces 44a, 46a keep large contact stresses from forming in the spring 40 when the spring 40 is flexed. The bosses 44, 46 are located centrally on the interior portion 16 of the lower implant body 12 such that they are oriented parallel to the anterior-posterior axis 38 when the implant 5 is implanted in the patient to facilitate movement of the translating body 18 along the anterior-posterior axis.

Figure 15:
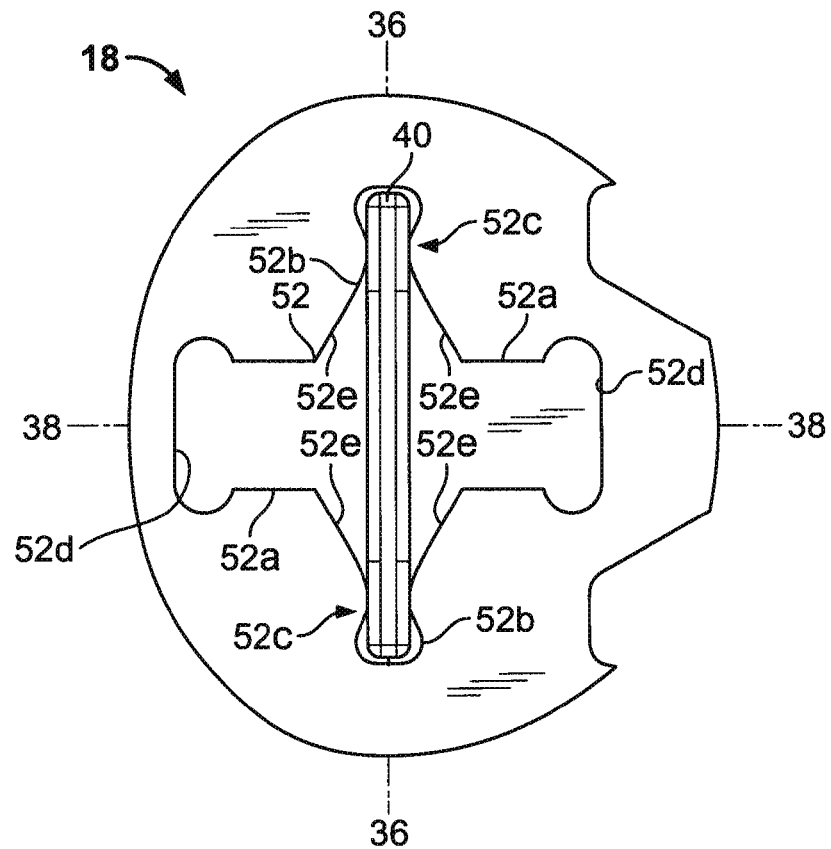
FIG. 15 is a bottom plan view of the lower surface of the translatable member of the implant of FIG. 1 showing the biasing member disposed in a recess of the translatable member.
Figure 16:
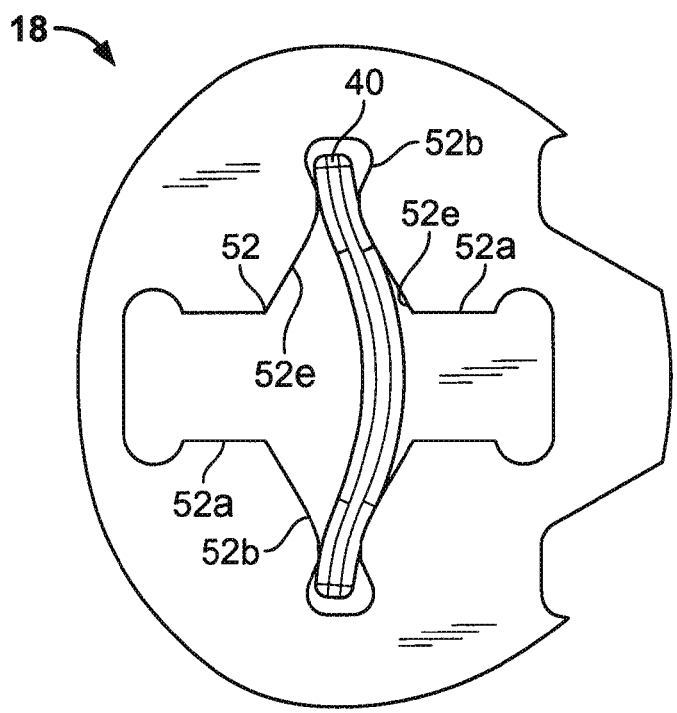
FIG. 16 is a bottom plan view of the translatable member of FIG. 15 showing the biasing member in a flexed or biased orientation corresponding with the orientation of the implant shown in FIGS. 11 and 12.
Figure 17:
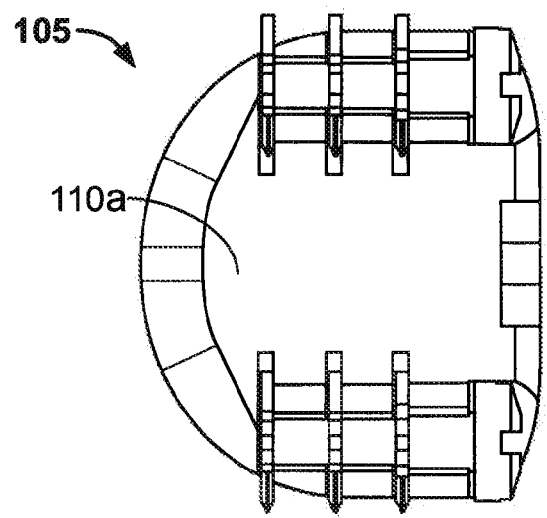
FIG. 17 is a top plan view of an alternate embodiment of an implant according to the present invention.
Figure 18:
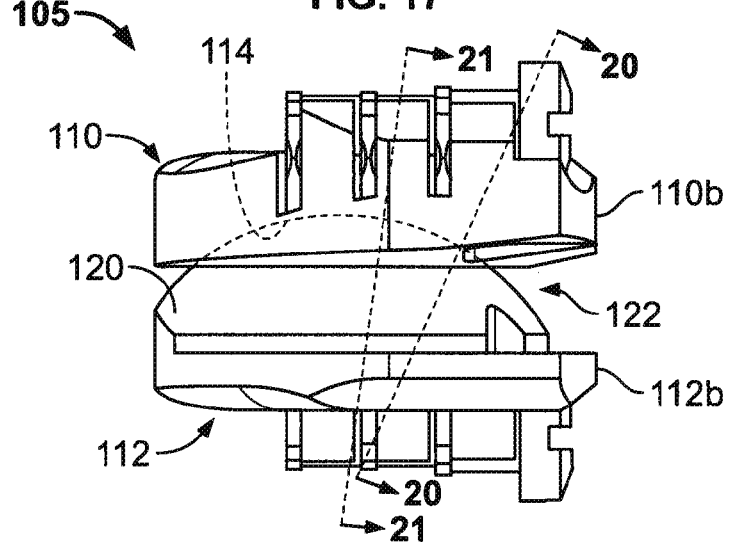
FIG. 18 is a side elevational view of the implant of FIG. 17.
Figure 19:
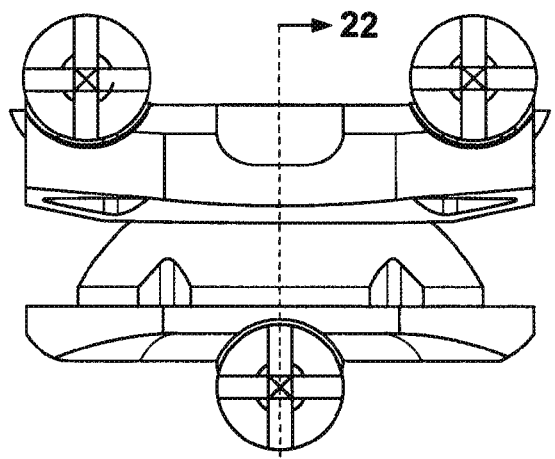
FIG. 19 is a rear elevational view of the implant of FIG. 17.

As shown in FIGS. 8, 15 and 16, the spring 40 and the bosses 44, 46 are disposed within a recess portion 52 formed in the translatable member 18. The recess 52 is preferably cross-shaped with an anterior-posterior extending portion 52a and a laterally extending portion 52b to contain the spring 40 and bosses 44, 46. The laterally extending portion 52b of the cross-shaped recess 52 has narrow ends 52c to securely capture the spring 40 therein. The anterior-posterior extending portion 52a of the recess 52 is sized to house the bosses 44, 46 of the lower implant body member 12. The anterior-posterior portion 52c is slightly elongated to provide additional clearance for the bosses 44, 46 which allows the articulation member 18 to move anteriorly or posteriorly with respect to the lower implant body 12. In a preferred form, the translatable member 18 is manufactured to allow between 0.5 mm to 0.75 mm total translation. In a preferred form, the translatable member 18 may translate 0.3 mm in either an anterior or a posterior direction. The entire length of the anterior-posterior portion 52a of the translatable member recess 52 is approximately 2 mm.

Stop members, such as abutment surfaces 52d at either end of the anterior-posterior portion 52a are provided to abut with the outer opposite surfaces 44b, 46b of the bosses 44, 46 (see FIG. 13). These surfaces 52d and 44b, 46b provide outer limits on the range of motion of the articulation member 18. As shown in FIG. 7, the recess 52 preferably has protruding ledges 54 formed near the lower face 18a of the translating member 18 along the edges of the anterior-posterior portion 52a of the recess 52 and located on either side of the laterally extending portion 52b of the recess 52. These ledge portions 54 interface with corresponding recessed channels 44c, 46c in both of the bosses 44, 46 (see FIG. 12). This structure keeps the articulation member 18 from being separated from the lower implant body 12. The enlarged end portions of the anterior-posterior portion 52a of the recess 52 are provided primarily for ease of manufacturing. The laterally extending portions 52b of the recess 52 have widened portions defined by side walls 52e to provide the spring 40 with room to flex in both the anterior and posterior directions, as shown in FIG. 16.

Figure 10:
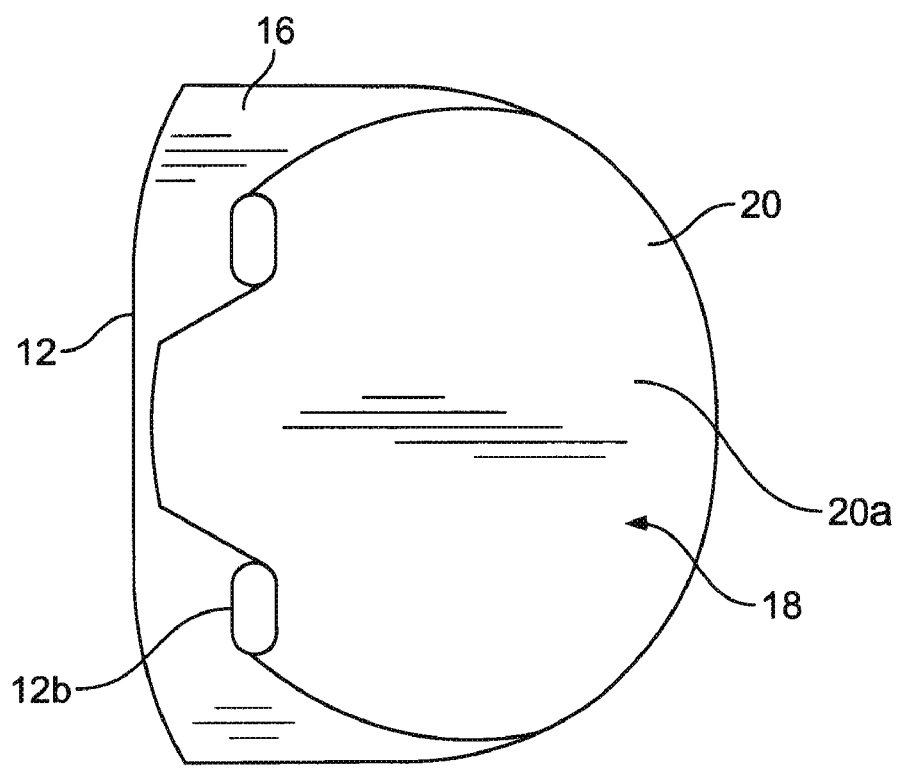
FIG. 10 is a top plan view of the implant of FIG. 9.

As shown in FIGS. 13 and 15, the spring 40 is in an unflexed or unbiased position. Forces on the implant 5 caused by flexion or extension of the joint cause the translatable member to translate with respect to the lower implant body 12, as shown in FIGS. 10 and 11. The movement of the translatable member 18 urges the spring 40 against the inner facing surface 44a of the posterior boss 44 while the outer ends of the spring 40 are brought posteriorly along with the translatable member 18 as shown in FIGS. 11, 13 and 15. A similar result occurs when forces on the implant 5 cause the translatable member 18 to move anteriorly so that the ends of the spring 40 are moved anteriorly and the center of the spring 40 is urged against the inner facing surface 46a of the anterior boss 46. Thus, as can be seen, the spring 40 provides resistance to the translation of the translatable member 18. This feature provides for gentle and natural articulation of the implant 5, which improves the performance of the joint.

Another advantageous feature of the present invention is that the biasing member urges the translatable member 18 back to its initial position once the translating force has been removed from the implant body. As the spring 40 will naturally tend to return to its original shape once the translating force has been removed from the implant body, the spring 40 will return to its unbent or unbiased, elongated shape, which forces the translatable member 18 back to its initial position. This self-centering feature mimics the natural dynamics of a healthy joint and provides the user increased comfort and functionality.

Abrupt stops in the translation of the translatable member 18 are to be avoided as they can be uncomfortable and even dangerous to the user. Referring now to FIGS. 13 and 15, the biasing member may be operable to keep the translating member 18 from abruptly stopping at the limits of its range of travel. Instead of relying entirely upon the abutment surfaces 52d of the translatable member 18 contacting with the corresponding outer surfaces 44b, 46b of the bosses 44, 46, the spring 40 may provide sufficient resistance to the translation of the translatable member 18 to stop translation of the translatable member 18 before it reaches its outer limit of travel. The outer surface 44b, 46b and abutment surfaces 52d then act primarily as a back-up to the biasing member should the biasing member fail, or should the forces acting on the translating member 18 be sufficient to overcome the reaction force provided by the biasing member at the outer limit of travel of the translatable member 18. It follows that the spring 40 will slow the translation of the translatable member 18 which may cushion or prevent abrupt stops in translation.

As shown in FIG. 12, the upper implant body 10 translates along with the translatable member 18 with respect to the lower implant body 12 due to the interaction between the convex articulation surface 20a and the concave articulation surface 14a. The translatable member 18 is preferably a moveable articulation member having an articulation surface 20a disposed between the first and second articulating implant members and connected to at least one of the first and second articulating members such that the member may translate with respect to at least one of the first and second articulating members. In this form, the implant may articulate as well as translate simultaneously. This combination of articulation and translation provides for a more natural movement of the joint and increases the range of motion thereof. Alternatively, the translating member 18 could be a non-articulation member such that the upper and lower implant bodies merely translate with respect to one another without any additional articulation.

Although in the embodiments disclosed herein illustrate a translating member disposed between the implant bodies, the translating body could be omitted entirely while retaining the biasing member to allow biased translation between upper and lower implant bodies. In addition, although the embodiments having described the biasing member as a leaf-type spring 40, the biasing member could also be a variety of resilient members, such as a coil spring, or other resilient material such as a polymer, a composite, or a gel.

In an alternate embodiment in accordance with the present invention, such as illustrated in FIGS. 17-22, an artificial disc device 105 comprises an articulation interface 122 with a complex configuration to provide for more natural articulation of the intervertebral joint. The embodiment described currently is similar in most aspects to the embodiment described in FIGS. 1-16, except that the articulation member 118 is fixed, as opposed to being a translatable member. Despite being fixed, the articulation interface 122 provides for rotation and translation between the vertebrae due to the interactions between the concave and convex articulating surfaces 114a, 120a.

In general, the upper implant body 110 includes a concave portion 114 having an articulation surface 114a. The concave articulation surface 114a preferably has multiple radii of curvature in at least one plane. As shown in FIG. 22, the concave articulation surface 114a is divided into a posterior portion 114b and an anterior portion 114c in the sagittal plane, with a line interface 114d generally located between the posterior and anterior portions 114b, 114c. The posterior portion 114b has a first radius in the sagittal plane, and the anterior portion 114c has a second, different radius. The anterior portion 114c is preferably slightly shallower than the posterior portion 114b, such that the articulation interface 122 provides for sliding in extension, i.e. when the anterior ends of the upper and lower implant bodies 110b, 112b are distracted apart from each other. The articulation interface 122 also provides for rotation between the implant bodies 110, 112 when the intervertebral joint is in extension. In a preferred form, the first radius of curvature is 0.252 inches and the second radius of curvature is 0.313 inches. The line interface 114d comprises the location where the first and second radii of curvature meet, and extends generally laterally between the posterior and anterior portions 114b, 114c. The radius of curvature of the concave articulation surface 114a in the coronal plane is preferably equal to the first radius of curvature or 0.252 inches.

The lower implant body 112 includes a convex portion 120 with an articulation surface 120a. The convex articulation surface 120a preferably has a single radius of curvature in both the sagittal and coronal planes, such that the surface 120a has a generally spherical shape. The radius of curvature of the convex articulation surface 120a is preferably equal to the first radius, or 0.252 inches in the illustrated embodiment. The convex articulation surface 120a matingly engages the concave articulation surface 114a to provide the articulation interface 122 between the upper and lower bodies 110, 112. Specifically, in a neutral orientation, correlating to an unflexed or unextended position of the joint, the convex articulation surface 120a engages the posterior portion 114b of the concave articulation surface 114a. This position correlates to a neutral or initial position of the implant, wherein the implant members are aligned (i.e., not staggered with respect to one another.)

As the intervertebral joint is extended, the concave and convex articulation surfaces 114a, 120a will slide against each other and the upper and lower implant bodies 110, 112, will pivot or rotate with respect to one another without substantial translation. As the anterior ends of the implant bodies 110b, 112b begin to open up and distract apart from each other, the concave articulation surface 120a will continue to pivot on the convex articulation surface 114a until the convex articulation surface 114a slips past the line interface 114d and slides into the anterior portion 114c of the concave articulation surface 114a. In this orientation, the convex articulation surface 120a will be primarily in mating contact with the anterior portion 114c of the concave articulation surface 114a. By sliding into the anterior portion 114c, the implant bodies 110, 112 are allowed to translate between 1-2 mm with respect to each other, which is believed to keep the implant 105 from binding and the facet joints from being overloaded. Upon return of the joint towards its neutral orientation through flexion, the convex articulation surface 120a will slide back into its initial position in engagement with the posterior portion 114b and will continue to pivot with respect to the concave articulation surface 114a within the posterior portion 114b. The implant will tend to return to the neutral orientation under normal loading, because it is the most compact orientation of the implant. This configuration is advantageous, because the articulation surfaces will return to their initial "centered" orientation when the joint returns to its neutral position, unlike known prior art implants. This keeps the upper and lower implant bodies 110, 112 from becoming staggered, such that one of the bodies is positioned anteriorly or posteriorly of the other when the spinal joint is in a neutral position.

Figure 20:
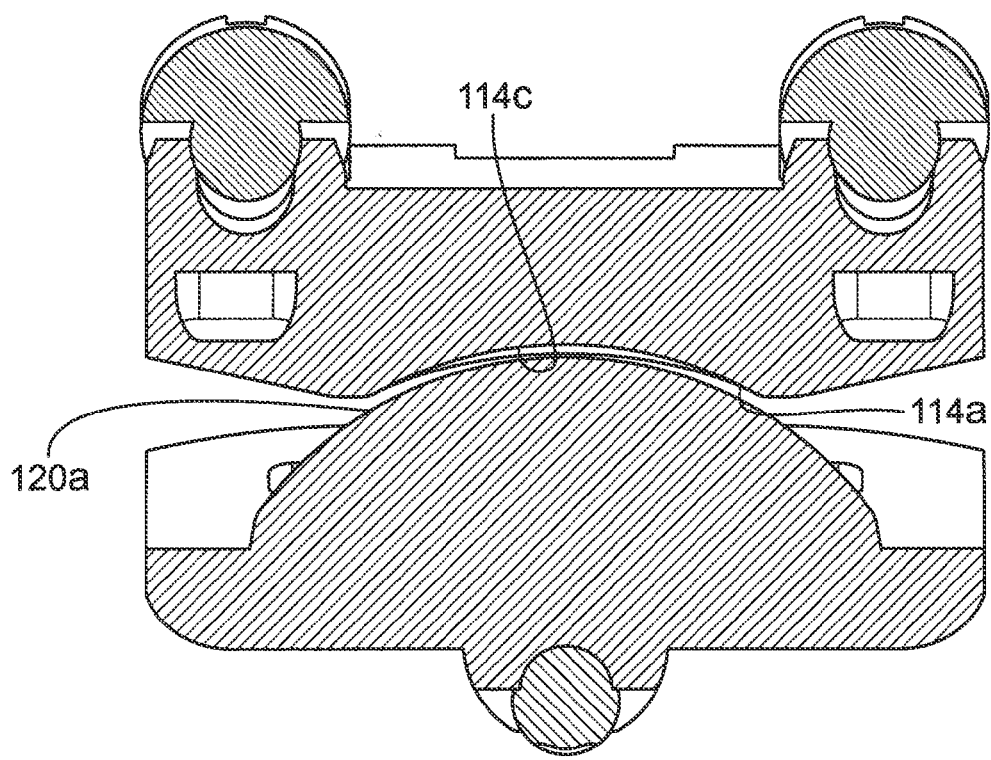
FIG. 20 is a cross-sectional view of the implant of FIG. 17 taken along the line 20-20.
Figure 21:
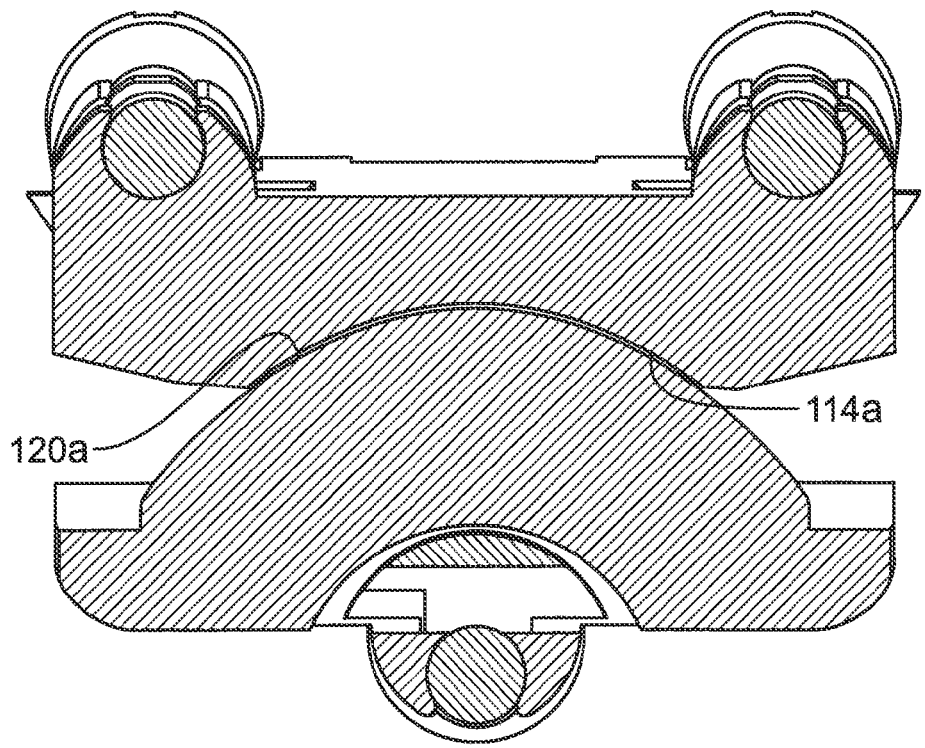
FIG. 21 is a cross-sectional view of the implant of FIG. 17 taken along the line 21-21.

With the configuration described immediately above, the articulating surfaces are subject to approximately 50% less wear than an articulation interface having matching radii of curvature. As shown in FIGS. 20 and 22, the convex articulation surface 120a only contacts one of the posterior and anterior portions 114b, 114c of the concave articulation surface 114a at one time. Thus, the contact area between the articulation surfaces 114a, 120a is substantially smaller than that of an implant with a matching articulation interface. Thus, this configuration will increase the lifespan and reduce the likelihood of failure of the implant. In addition, as wear particles from the implant 105 can cause adverse reactions for the patient, the implant as described above further increases the safety and comfort of the implant 105. Further, the range of motion provided by the implant described above also helps to prevent facet joint loading, which can lead to further complications for the user.

Although the embodiment described above has been described to allow translation of the implant bodies when the intervertebral joint is in extension, it could also be configured to provide translation in flexion. Further, translation could also be provided in other directions other than the anterior-posterior direction.

Figure 23:
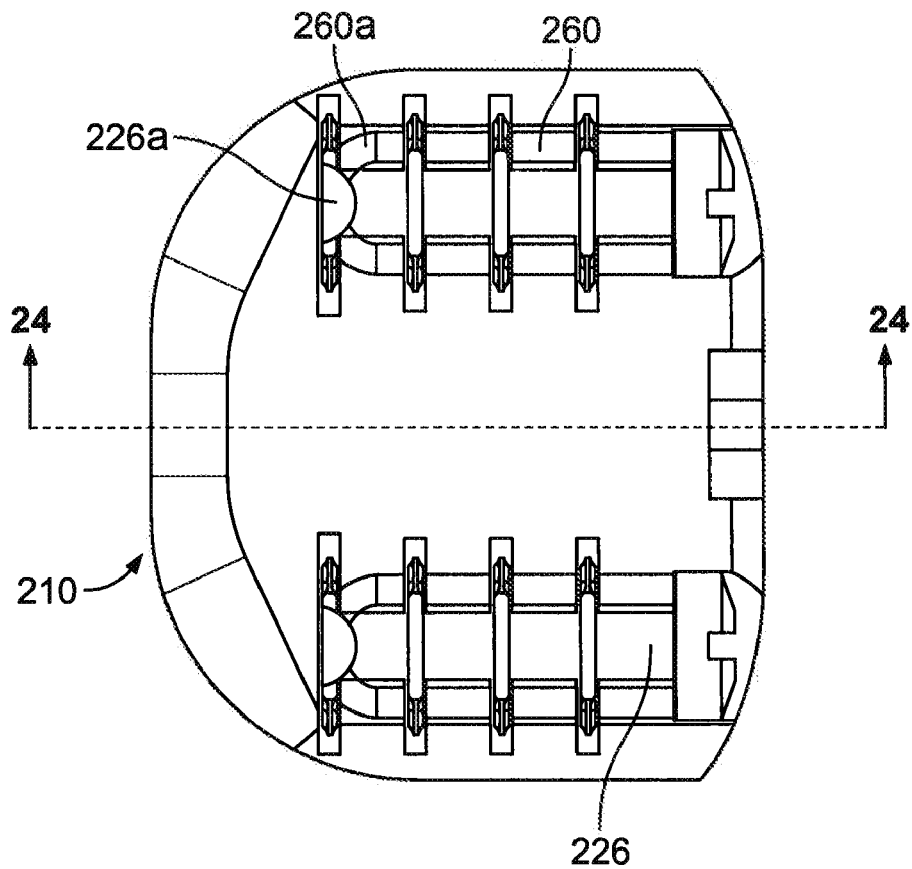
FIG. 23 is a top plan view of an alternate embodiment according to the present invention having alternate securing structure for improving securing strength thereof and for easing insertion of the implant.
Figure 24:
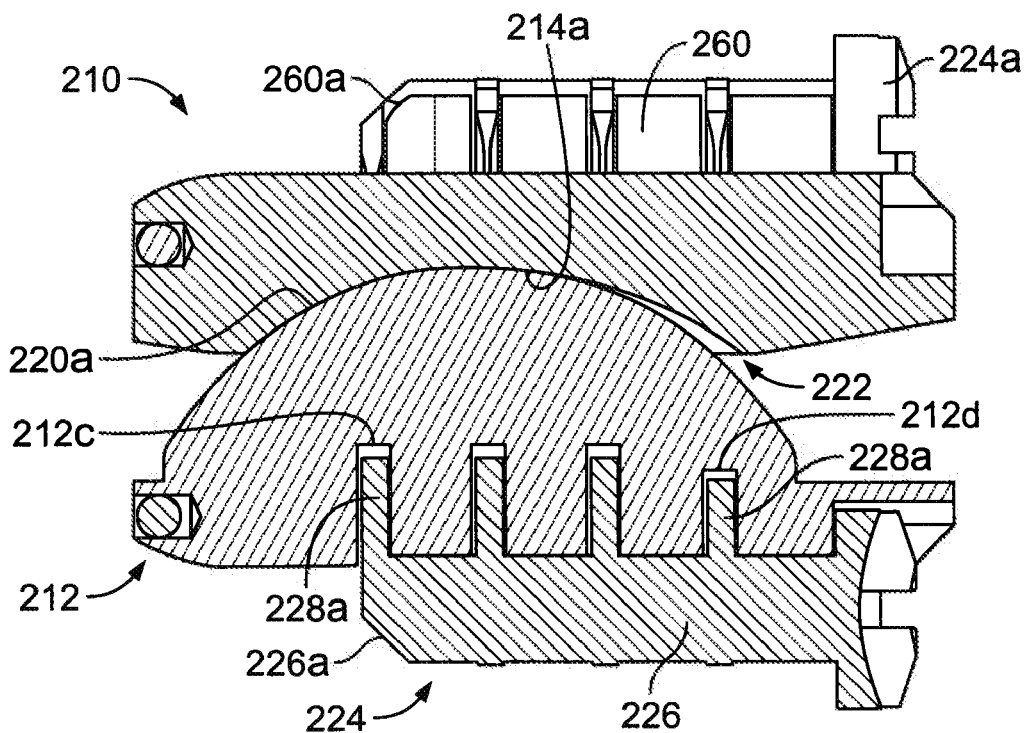
FIG. 24 is a cross-sectional view of the implant of FIG. 23 taken along the line 23-23 showing bone-engaging members of the lower securing member of varying size.
Figure 25:
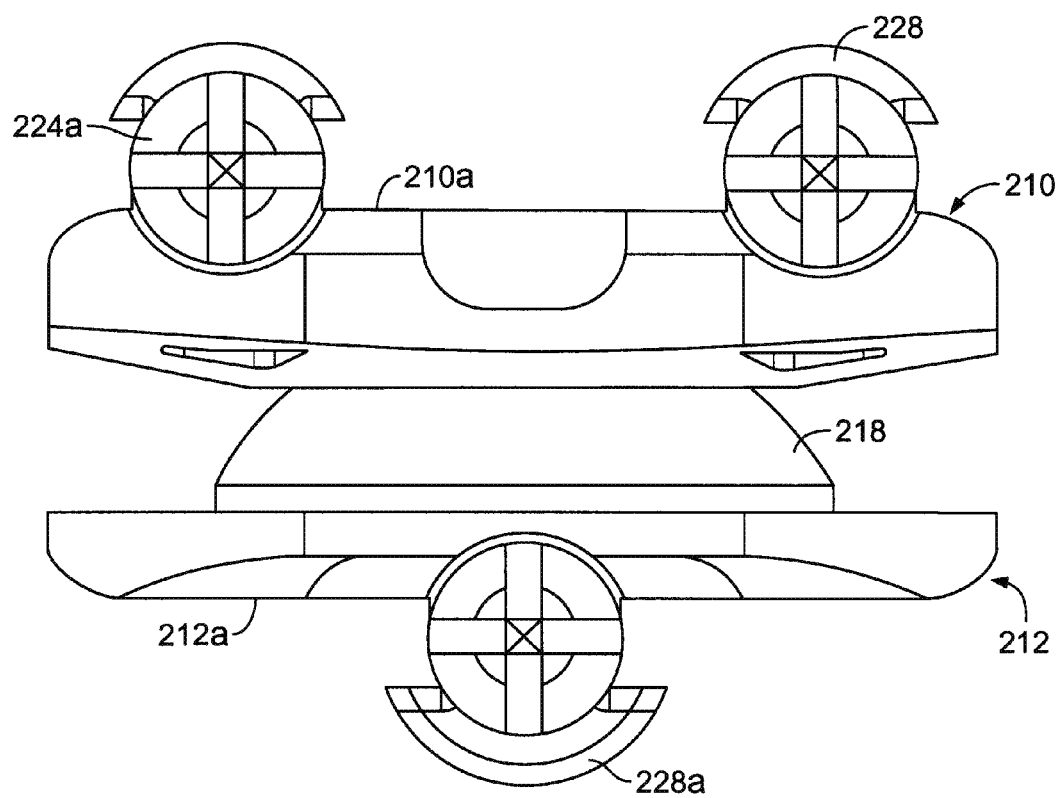
FIG. 25 is a rear elevational view of the implant of FIG. 23 taken along the line 22-22 showing a bone-engaging member of the lower securing member having a larger size than the bone-engaging members of the upper securing member for increasing the securing strength thereof.

An alternate embodiment in accordance with the present invention, such as illustrated in FIGS. 23-25, takes the form of an artificial disc device similar to the device of FIGS. 17-22, with an alternate arrangement of the securing members 224. In this form, the securing members are configured for ease of insertion and improved securing strength. In addition, the securing members 224 are mounted to the upper and lower bearing members 210, 212 at locations where the bearing members have an enlarged profile. This allows the bone-engaging portions 228, 228a to be disposed within the bearing members 210, 212 with the securing members 224 in an undeployed orientation, such as that shown in FIGS. 23 and 24.

In the present embodiment, securing members 224 preferably include a rotary shaft 226 with a tapered or beveled end 226a opposite the shaft head 224a that angles outwards and away from the outer bearing surfaces 210a, 212a in a direction opposite the insertion direction. The retaining members 260, which grippingly engage the securing members 224, also have a tapered or beveled leading end 260a to promote ease of insertion of the implant. Thus, the leading ends of the securing members 224 and the retaining members 260 are contoured to keep the implant from binding on the vertebrae or adjacent tissues during insertion.

Also in accordance with the present invention, the securing members may have various sizes and shapes to maximize securing strength thereof and to maximize the compressive strength of the implant itself. Where only one securing member 224 is present, such as on the lower bearing member 212 as shown in FIGS. 24 and 25, the fin size is preferably increased to increase the amount of surface area in contact with the adjacent vertebra when the securing member 224 is in a deployed orientation. Where two or more securing members 224 are utilized on a bearing member, the fin size may be smaller, as more fins 228, 228a are in engagement with the adjacent vertebra. In addition, the number of fins 228, 228a disposed on each securing member 224 may be increased or decreased depending on the level of gripping power desired and the size of the implant. Larger implants will generally utilize securing members 224 with more fins 228, 228a, while smaller implants may use fewer fins.

The bone-engaging members disposed on each securing member 224 may have the same general size, such as shown in FIG. 7, or the bone-engaging members may have different sizes. For example, the anterior-most fin 228a of the lower securing member 224 shown in FIG. 24 has a lower profile than then other fins 228a disposed thereon. The bone-engaging members are preferably sized such that they will engage with cortical bone when deployed into the vertebrae, which offers greater support to the bone-engaging members to resist expulsion of the implant from the intervertebral space.

Another reason for utilizing different size bone-engaging members is to maximize the structural integrity of the implant. Each bone-engaging member recess, such as lower fin recesses 212c shown in FIG. 24, protrudes axially in the cephalic direction. Each recess must not protrude too far into the implant body 212 to keep body from losing structural integrity. If the cross-section of the body gets too narrow, stress concentrations on the narrow portion may cause the implant body to crack or break when under load. Thus, as shown in FIG. 24, the anterior-most recess 212d, as well as the bone-engaging member 228a, are shortened where the bearing member 212 has a narrower profile.

The securing members are preferably located on the upper and lower bearing members 210, 212 where the bearing members have an enlarged profile. For example, on the upper bearing member 210, the securing members 224 are mounted axially adjacent the concave bearing surface 214, i.e., near the outer lateral sides of the bearing member. In this location, the implant body 210 has a larger profile compared with the central portion of the body, which is thinner due to the central location of the concave articulation surface 214a, which forms part of the articulation interface 222. This configuration allows the bone-engaging members 228 to be disposed at least partially within the implant body 210 prior to deployment. It is preferred that the bone-engaging members are disposed within the implant body because they are prevented from protruding through the inner surface of the implant body, where they may interfere with range of motion of the implant or damage the inner surfaces of the implant bodies 210, 212 prior to deployment of the securing members 224.

Similarly, the lower securing member 224 is mounted to the lower bearing member 212 in substantial alignment with the convex bearing surface 218 such that the bone-engaging members are disposed in an axially enlarged portion of the body 212 with the securing member 224 in an undeployed orientation, as shown in FIG. 25. The convex bearing surface 218 provides the axially enlarged central portion of the lower bearing member 212, providing sufficient space for the fins 228a to be disposed within the body of the lower bearing member. This configuration also allows for the outer lateral sides of the lower bearing member 212 to have a thinner profile, as shown in FIG. 25. This allows for a larger gap between the inner facing surfaces of the upper and lower bearing members 210, 212. This gap allows the upper and lower bearing members 210, 212 to rotate and pivot with respect to one another to allow for natural movement of the intervertebral joint. Thus, in the form shown in FIGS. 23-25, the securing members 224 are oriented and configured to provide an implant with sufficient load-bearing capacity and increased securing strength between the securing members 224 and the adjacent bone to resist expulsion of the implant.

The articulating joint surfaces described herein are preferably a combination of PEEK articulating on PEEK, PEEK on carbon reinforced (CR) PEEK, or CR PEEK on CR PEEK.

It is preferable that the radiolucent implant includes one or more radiopaque markers which will show on up an X-ray image to assist the surgeon in positioning the implant during surgery. The preferred material for these markers is tantalum. Typically these markers will be encased in predetermined locations in the implant at their periphery. Coatings which show up on imaging as a subtle outline of the implant device may also be used.

It is also preferable, although not necessary, that the implants disclosed herein include a layer of osteo-conductive or osteo-inductive surfaces or coatings on those implant surfaces in contact with bone or tissue that will assist in securing the implant in a predetermined location. Typically this will occur through boney integration of the bone with the coating or implant surface. Examples of such coatings are hydroxyapatite, calcium phosphates such as tricalcium phosphate, or porous titanium spray.

The implant devices disclosed herein are particularly suited as intervertebral disc replacements for all or a portion of the natural intervertebral disc. The devices have minimal structural parts and are preferably manufactured from specialized materials that are substantially radiolucent such as PEEK or Carbon-Fiber PEEK in both their structural and joint articulating portions.

In other forms of the invention, the implant may comprise a pharmacological agent used for treating various spinal conditions, including degenerative disc disease, spinal arthritis, spinal infection, spinal tumor and osteoporosis. Such agents include antibiotics, analgesics, anti-inflammatory drugs, including steroids, and combinations thereof. Other such agents are well known to the skilled artisan. These agents are also used in therapeutically effective amounts. Such amounts may be determined by the skilled artisan depending on the specific case.

The pharmacological agents, if any, are preferably dispersed within the implant for in vivo release. The pharmacological agents may be dispersed in the implant by adding the agents to the implant when it is formed, by soaking a formed implant 5 in an appropriate solution containing the agent, or by other appropriate methods known to the skilled artisan. In other forms of the invention, the pharmacological agents may be chemically or otherwise associated with the implant. For example, the agents may be chemically attached to the outer surface of the implant.

In addition, the invention described herein may also be applied to other motion preserving implants, such as those with articulating surfaces, including nucleus replacement implants. Moreover, the concepts and methods described herein may be implemented in other weight-bearing joint implants, such as ankle, knee, or hip joint implants.

Generally, the various systems and methods described herein allow for an implant, such as an artificial disc, to be properly sized, implanted and secured in an intervertebral space with the disc having a bearing interface that preserves motion between the upper and lower vertebrae between which the disc is implanted and secured. In each form described herein, a trial spacer, such as one disclosed in U.S. patent application Ser. No. 11/856,667, may be used to assess the size of the intervertebral space so that an appropriately sized disc implant can be selected. The trial spacer can also be used to assist in generating features in the vertebrae and/or end plates thereof for a securing mechanism that holds and retains the disc implant in the intervertebral space.

While the invention has been described with respect to specific examples including presently preferred modes of carrying out the invention, those skilled in the art will appreciate that there are numerous variations and permutations of the above described systems and techniques that fall within the spirit and scope of the invention as set forth in the claims.

What is claimed is:

1. A weight-bearing implant comprising:
a first bearing member;
a body of the first bearing member having an outer bearing surface;
a second bearing member;
a body of the second bearing member having an outer bearing surface;
a translatable member disposed between the first and second bearing members having a predetermined position with respect thereto;
a resilient connection between the translatable member and at least one of the first and second bearing members comprising a biasing member operably connected to the translatable member to allow the translatable member to translate along the one bearing member and to resist translation of the translatable member along the one bearing member and to bias the translatable member towards the predetermined position thereof; and
bearing surfaces of the translatable member and the other bearing member that engage one another and allow for relative polyaxial motion therebetween with the resilient connection permitting the bearing surfaces to shift relative to the one bearing member to allow the relative polyaxial motion between the other bearing member and the translatable member to occur at different positions along the one bearing member;
wherein the translatable member comprises a recess portion with the biasing member disposed at least partially therein and operably connected to the second bearing member to provide the resilient connection between the translatable member and the second bearing member.

2. The weight-bearing implant of claim 1, wherein the bearing surfaces of the translatable member and the other bearing member comprise dome-shaped surfaces, and the implant further comprises:
an arcuate interface formed by the bearing surfaces of the translatable member and the other bearing member to allow the translatable member and the other bearing member to undergo polyaxial articulation with respect to one another and together with the resilient connection permit the polyaxial articulation to occur at different positions along the one bearing member.

3. The weight-bearing implant of claim 1, further comprising:
an opposite bearing surface of the translatable member opposite the dome-shaped bearing surface;

an inner facing bearing surface of the at least one bearing member; and a sliding interface formed by the opposite bearing surface of the translatable member and the inner facing articulation surface that allows the translatable member to translate linearly along the at least one bearing member.

4. The weight-bearing implant of claim 1, wherein the resilient connection allows the translatable member to translate linearly along a predetermined first direction and the biasing member is a flat spring having a longitudinal axis disposed generally orthogonal to the first direction.

5. The weight-bearing implant of claim 4, wherein the one bearing member comprises a spring-receiving portion including a channel for receiving the spring therein and offering support to opposing sides thereof.

6. An intervertebral implant for being inserted between adjacent upper and lower vertebrae, the intervertebral implant comprising:

an upper body;

a lower body;

an articulation interface between the upper and lower bodies;

a concave articulating surface of the articulation interface having first and second sections having first and second radii of curvature respectively in at least one plane corresponding with a sagittal plane of the upper and lower vertebrae, wherein the first radius of curvature is smaller than the second; and a convex articulating surface of the articulation interface having a spherical configuration including a single radius of curvature corresponding substantially with the first radius of curvature of the first section of the concave articulating surface in the sagittal plane, such that the articulation interface provides for polyaxial pivoting as well as translation of the upper and lower bodies with respect to each other in an anterior-posterior direction to provide for natural movement of the upper and lower vertebrae in flexion and extension.

7. The intervertebral implant of claim 6, wherein the concave articulating surface is disposed on the upper body.

8. The intervertebral implant of claim 7, wherein the convex articulating surface is disposed on the lower body.

9. The intervertebral implant of claim 6, wherein the first section of the concave articulation surface is located relatively posteriorly and the second section of the concave articulation surface is located relatively anteriorly to allow the upper and lower bodies to translate with respect to one another with the adjacent vertebrae in extension.

10. The intervertebral implant of claim 9, wherein the first and second sections of the concave articulation surface intersect one another, such that the concave articulation surface includes a line interface wherein the radius of curvature of the concave articulation surface changes between the first and second radii of curvature of the first and second sections.

11. The intervertebral implant of claim 8, wherein the line interface is located generally at a midpoint of the articulation interface.

12. The intervertebral implant of claim 6, wherein the concave and convex articulation surfaces have the first radius of curvature in a coronal plane.

13. The intervertebral implant of claim 6, wherein the articulating surfaces have a neutral orientation with the convex articulation surface in contact with a portion of the first section of the concave articulating surface having the first radius of curvature in the sagittal plane for providing a compact configuration of the implant which operates to self-center the articulation surfaces.

14. An intervertebral implant for being inserted between adjacent upper and lower vertebrae, comprising:

upper and lower bearing members each having a body and an outer bearing surface for facing the adjacent vertebrae;

inner arcuate bearing surfaces of the bearing members;

an articulation interface between the inner arcuate bearing surfaces to allow polyaxial articulation between the upper and lower bearing members;

a rotary securing member mounted to each of the bearing members, each of the rotary securing members including a rotary shaft having a longitudinal axis that is oriented to extend along the outer bearing surface of the corresponding bearing member for being turned to secure the bearing member to the adjacent vertebral bone;

the rotary shaft of the securing member having a bone-engaging portion fixed thereon to extend transversely therefrom to allow the rotary shaft of the rotary securing member to be rotated from an undeployed orientation with the bone-engaging portion out of engagement with the adjacent vertebral bone and a deployed orientation with the bone-engaging portion in engagement with the adjacent vertebral bone;

the rotary shaft being configured such that rotation thereof does not cause the rotary shaft to advance along the outer bearing surface of the bearing member; and each rotary securing member mounted to the bearing members at a body portion thereof wherein the body of the bearing member has an enlarged profile in an axial direction so that in the undeployed orientation the bone-engaging portion fixed on the rotary shaft is at least partially disposed within the enlarged profile body portion of the bearing member.

15. The intervertebral implant of claim 14, wherein the inner arcuate bearing surface of the lower bearing member comprises a convex bearing surface, and the rotary securing member mounted to the lower bearing member is substantially aligned with the convex bearing surface such that the bone-engaging portion of the securing member is disposed in an axially enlarged body portion of the lower bearing member body with the securing member in an undeployed orientation.

16. The intervertebral implant of claim 14, wherein the inner arcuate bearing surface of the upper bearing member comprises a concave bearing surface, and the rotary securing member mounted to the upper bearing member is disposed axially adjacent the concave bearing surface such that the bone-engaging portion of the securing member is disposed in an axially enlarged body portion of the upper bearing member body with the securing member in an undeployed orientation.

17. The intervertebral implant of claim 14, wherein at least one of the rotary securing members includes a plurality of bone-engaging portions each having a size fixed to the rotary shaft, wherein at least one of the plurality of bone-engaging portions has a size different than the other of the plurality of bone-engaging portions.

18. The intervertebral implant of claim 14, wherein the rotary shaft of each securing member is at least partially disposed within the enlarged profile body portion of the respective bearing member.

* * * * *